US011534158B2

(12) United States Patent
Khanicheh et al.

(10) Patent No.: US 11,534,158 B2
(45) Date of Patent: Dec. 27, 2022

(54) ENDOSCOPIC SUTURE CINCH

(71) Applicant: EnVision Endoscopy, Inc., Somerville, MA (US)

(72) Inventors: Azadeh Khanicheh, Somerville, MA (US); Amos Cruz, Wrentham, MA (US)

(73) Assignee: EnVision Endoscopy, Inc., Somerville, MA (US)

( * ) Notice: Subject to any disclaimer, the term of this patent is extended or adjusted under 35 U.S.C. 154(b) by 0 days.

(21) Appl. No.: 17/508,989

(22) Filed: Oct. 23, 2021

(65) Prior Publication Data
US 2022/0125426 A1 Apr. 28, 2022

Related U.S. Application Data

(60) Provisional application No. 63/104,585, filed on Oct. 23, 2020.

(51) Int. Cl.
*A61B 17/04* (2006.01)
*A61B 1/018* (2006.01)
*A61B 17/00* (2006.01)

(52) U.S. Cl.
CPC .......... *A61B 17/0487* (2013.01); *A61B 1/018* (2013.01); *A61B 17/0469* (2013.01); *A61B 17/0485* (2013.01); *A61B 2017/0034* (2013.01); *A61B 2017/00358* (2013.01); *A61B 2017/0488* (2013.01)

(58) Field of Classification Search
CPC ............ A61B 17/0487; A61B 17/0485; A61B 2017/0488; A61B 2017/00358; A61B 1/018
See application file for complete search history.

(56) References Cited

U.S. PATENT DOCUMENTS

| 5,499,991 A | 3/1996 | Garman et al. |
| 5,817,111 A | 10/1998 | Riza |
| 6,719,763 B2 | 4/2004 | Chung et al. |

(Continued)

FOREIGN PATENT DOCUMENTS

| AU | 670461 B2 | 7/1996 |
| CN | 1879556 B | 12/2010 |

(Continued)

OTHER PUBLICATIONS

Medtronic, "Simplicity Meets Security in Laparoscopic Suturing," retrieved from the Internet under https://www.merit.com/peripheral-intervention/access/renal-therapies-accessories/slip-not-suture-retention-device/#tab-id-2, on Oct. 27, 2021, 4 pages.

(Continued)

*Primary Examiner* — Tuan V Nguyen
(74) *Attorney, Agent, or Firm* — Nutter McClennen & Fish LLP

(57) ABSTRACT

A method cinches a suture. The method provides a cinch having a suture capturing portion configured to capture a suture, a cinch lock coupled with the suture capturing portion, and a cinch anchor having a lumen. The suture capturing portion is extended out of the lumen to capture the suture. The suture is captured by the suture capturing portion. The suture capturing portion is retracted into the lumen of the cinch anchor. The suture is cinched between the cinch lock and the cinch anchor.

20 Claims, 25 Drawing Sheets

(56) References Cited

U.S. PATENT DOCUMENTS

| | | |
|---|---|---|
| 6,755,843 B2 | 6/2004 | Chung et al. |
| 6,869,395 B2 | 3/2005 | Page et al. |
| 6,998,987 B2 | 1/2006 | Ishikawa et al. |
| 7,090,690 B2 | 8/2006 | Foerster et al. |
| 7,144,401 B2 | 12/2006 | Yamamoto et al. |
| 7,156,857 B2 | 1/2007 | Pasricha et al. |
| 7,530,985 B2 | 5/2009 | Takemoto et al. |
| 7,618,425 B2 | 11/2009 | Yamamoto et al. |
| 7,736,372 B2 | 6/2010 | Reydel et al. |
| 7,927,271 B2 | 4/2011 | Dimitriou et al. |
| 3,021,376 A1 | 9/2011 | Takemoto et al. |
| 8,287,556 B2 | 10/2012 | Gilkey et al. |
| 8,308,765 B2 | 11/2012 | Saadat et al. |
| 8,540,735 B2 | 9/2013 | Mitelberg et al. |
| 8,641,728 B2 | 2/2014 | Stokes et al. |
| 8,679,136 B2 | 3/2014 | Mitelberg |
| 8,758,405 B2 | 6/2014 | Zeiner et al. |
| 8,882,785 B2 | 11/2014 | DiCesare et al. |
| 8,945,180 B2 | 2/2015 | Roorda |
| 9,089,325 B2 | 7/2015 | Mitelberg et al. |
| 9,198,562 B2 | 12/2015 | Mitelberg et al. |
| 10,441,269 B1 | 10/2019 | Bonutti et al. |
| 2004/0158125 A1 | 8/2004 | Aznoian et al. |
| 2006/0282089 A1 | 12/2006 | Stokes et al. |
| 2006/0282090 A1 | 12/2006 | Stokes et al. |
| 2007/0010829 A1* | 1/2007 | Nobles ............... A61B 17/0487 606/148 |
| 2007/0239177 A1 | 10/2007 | Stokes et al. |
| 2008/0132919 A1 | 6/2008 | Chui et al. |
| 2012/0022560 A1 | 1/2012 | Ferreira |
| 2012/0143248 A1 | 6/2012 | Brecher et al. |
| 2012/0158023 A1* | 6/2012 | Mitelberg .......... A61B 17/0485 606/144 |
| 2012/0204865 A1 | 8/2012 | Filipi et al. |
| 2014/0171970 A1 | 6/2014 | Martin et al. |
| 2015/0157345 A1 | 6/2015 | Haack et al. |
| 2016/0045197 A1 | 2/2016 | Mitelberg et al. |
| 2019/0231347 A1 | 8/2019 | Bagaoisan et al. |
| 2019/0357899 A1* | 11/2019 | Gilbert ............... A61B 17/0485 |
| 2021/0093314 A1 | 4/2021 | Gilkey et al. |

FOREIGN PATENT DOCUMENTS

| | | |
|---|---|---|
| EP | 0588659 B1 | 11/1995 |
| JP | 2002159498 A | 6/2002 |
| JP | 2003070793 A | 3/2003 |
| JP | 2003284722 A | 10/2003 |
| JP | 3585951 B2 | 11/2004 |

OTHER PUBLICATIONS

Merit Medical, "Slip-Not Suture Retention Device," retrieved from the Internet under https://www.ncbi.nlm.nih.gov/pmc/articles/PMC7247903/ on Oct. 27, 2021, 5 pages.

Yamasaki Y., et al., "Dynamics of endoscopic snares: a new approach towards more practical and objective perfomance evaluation," Endosc. Int. Open, vol. 8, Issue 6, pp. E792-E795, Jun. 2020; retrieved from the Internet under https://hcpresources.medtronic.com/the-endo-stitch-suturing-device/brochure-benefits-of-v-loc-reload-for-use-with-the-endo-stitch-suturing-device, on Oct. 27, 2021, 7 pages.

Extended European Search Report for Application No. 19816026.9, dated Jan. 28, 2022, 12 pages.

International Search Report and Written Opinion for International Application No. PCT/US21/56384, dated Jan. 24, 2022 (7 pages).

International Search Report and Written Opinion for International Application No. PCT/US19/53877, dated Oct. 3, 2019 (11 pages).

\* cited by examiner

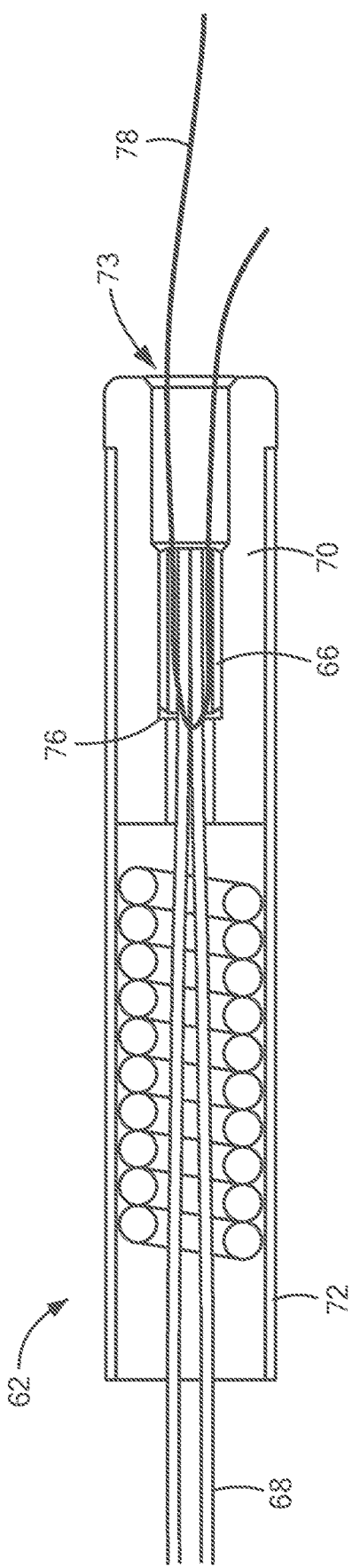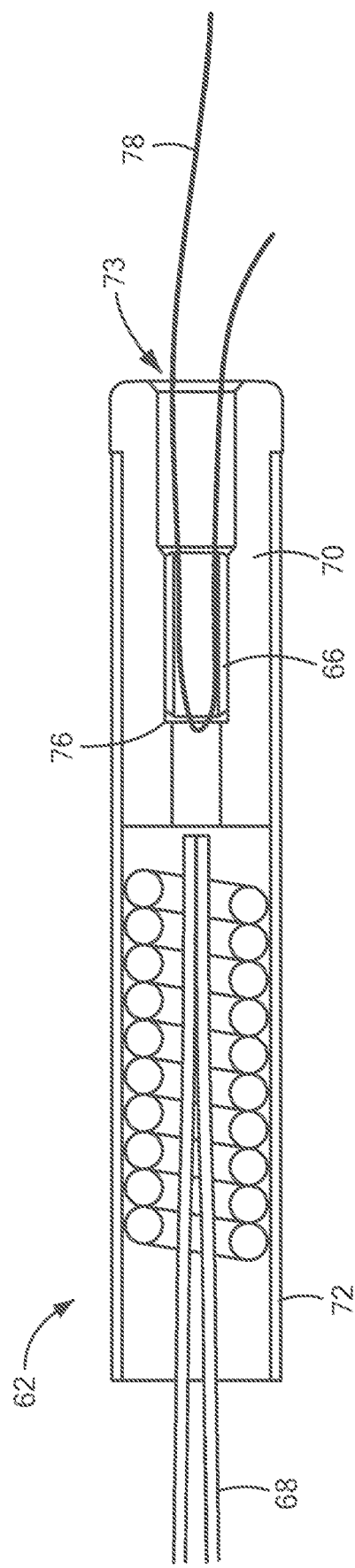

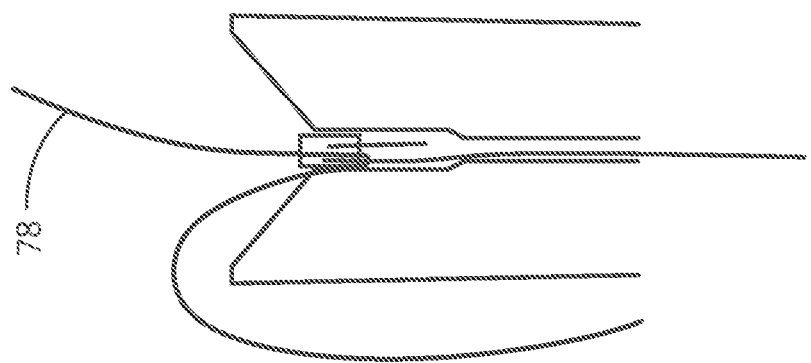
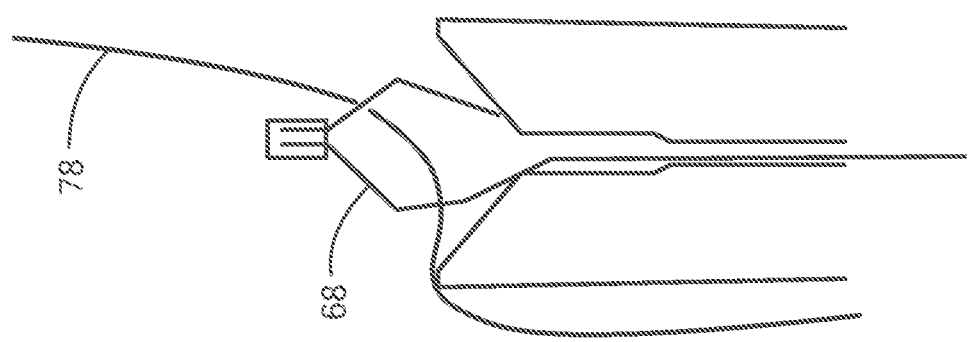
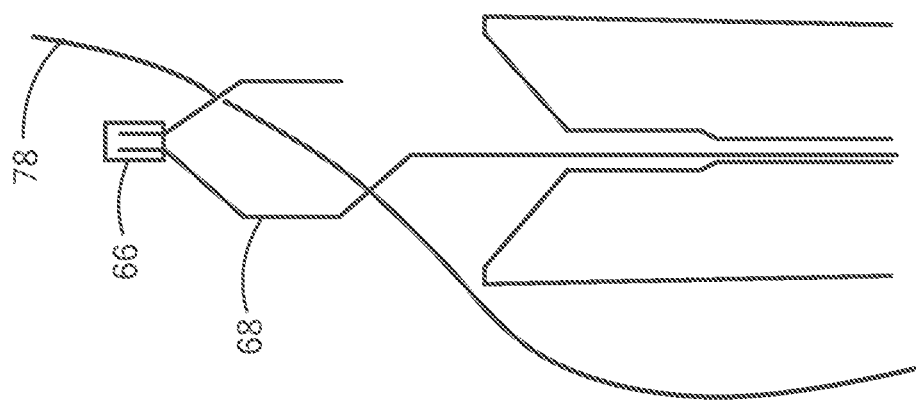
FIG. 12

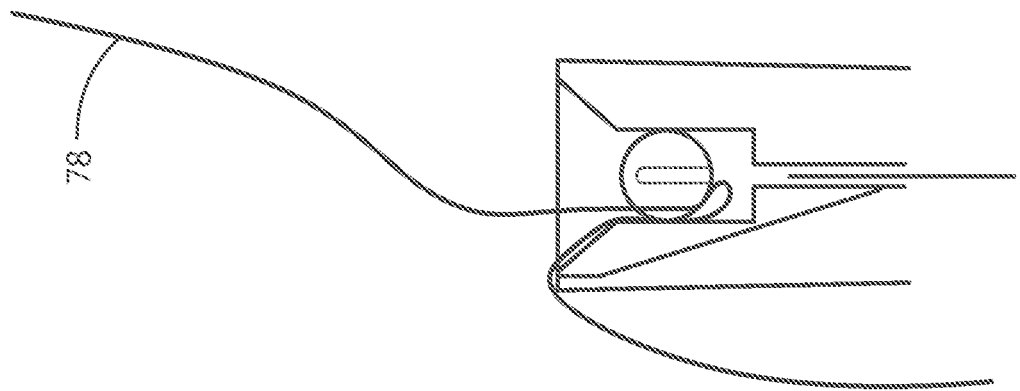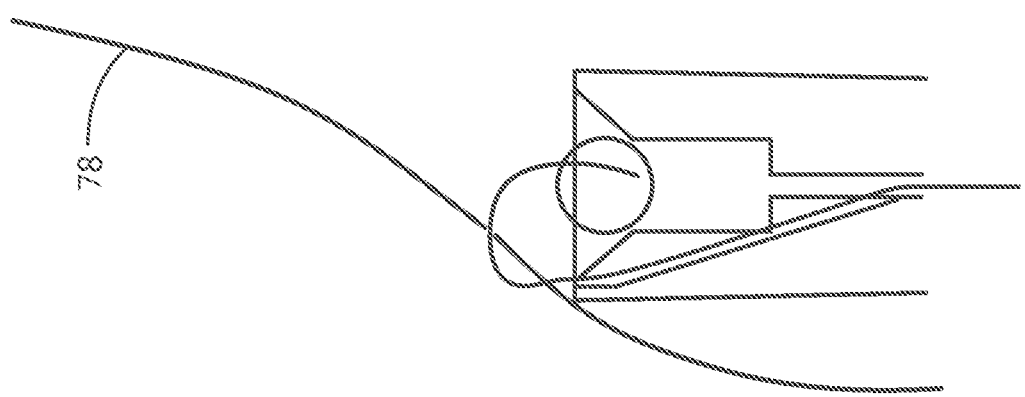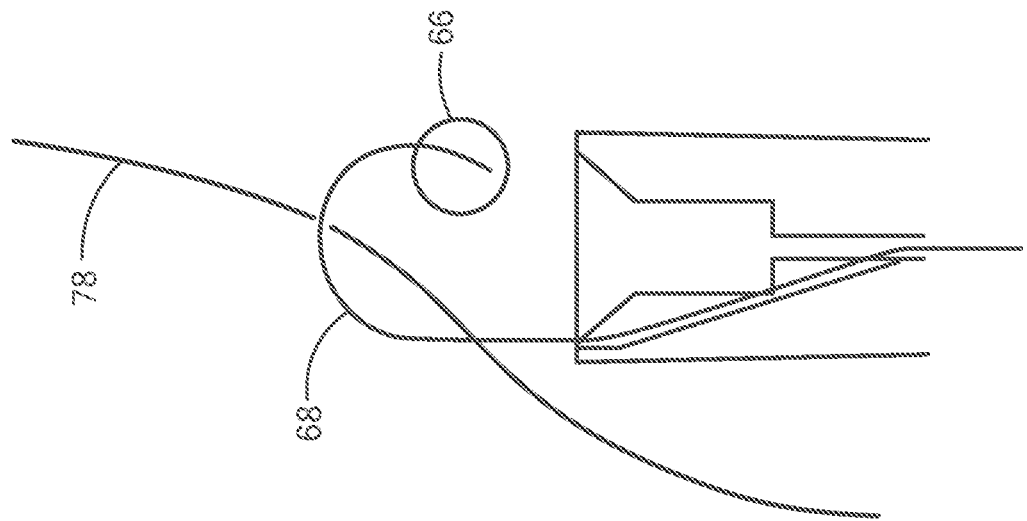
FIG. 13

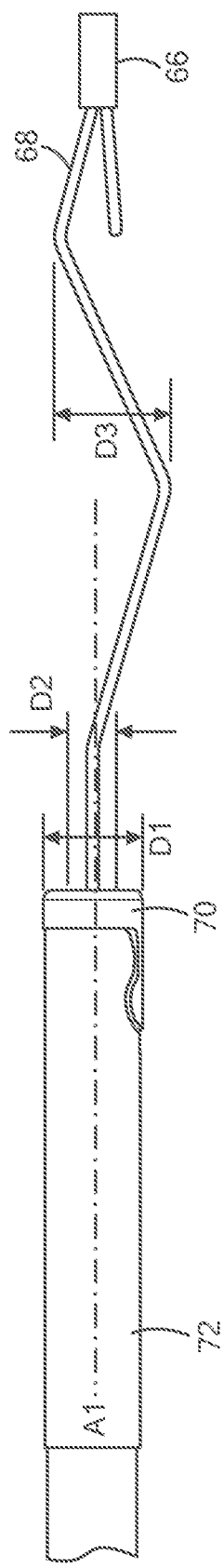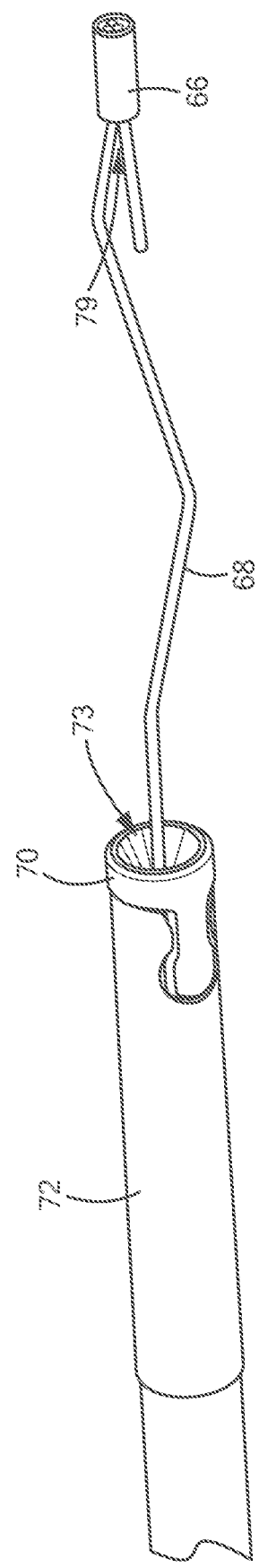
FIG. 15A
FIG. 15B

ENDOSCOPIC SUTURE CINCH

PRIORITY

This patent application claims priority from provisional United States patent application No. 63/104,585, filed Oct. 23, 2020, entitled, "ENDOSCOPIC SUTURE CINCH AND METHOD OF APPLYING," and naming Azadeh Khanicheh and Amos G. Cruz as inventors, the disclosure of which is incorporated herein, in its entirety, by reference.

STATEMENT AS TO FEDERALLY SPONSORED RESEARCH

This invention was made with government support under Award #1912944 by National Science Fund (NSF) SBIR Phase I. The government has certain rights in the invention.

FIELD OF THE INVENTION

Illustrative embodiments of the invention generally relate to endoscopic devices and, more particularly, the various embodiments of the invention relate to a suture cinch that is delivered through a working channel of the endoscope.

BACKGROUND OF THE INVENTION

A suture cinch is an alternative method to tying a knot to secure and anchor the suture for wound closure and tissue approximation. The cinch can be utilized for both interrupted and running stitches. Such cinching devices generally affix the suture by compression between two concentric cylindrical components. Currently available flexible endoscopy cinching devices load the suture into the cinch outside the patient's body. A free end of the suture (which is the end of the suture not attached to a needle) must be loaded into a cinching device outside the endoscope's working channel. Such devices often utilize a suture threader to thread the suture into a cinch, enabling the cinch to advance through a working channel of the endoscope.

Endoscopic snares usually are used to remove a polyp, adenoma, or foreign body from inside gastrointestinal tract through working channel of an endoscope. Alternatively, endoscopic hooks are currently used for endoscopic submucosal dissection.

SUMMARY OF VARIOUS EMBODIMENTS

In accordance with one embodiment of the invention, a method cinches a suture. The method provides a cinch having a suture capturing portion configured to capture a suture, a cinch lock coupled with the suture capturing portion, and a cinch anchor having a lumen. The suture capturing portion is extended out of the lumen to capture the suture. The suture is captured by the suture capturing portion. The suture capturing portion is retracted into the lumen of the cinch anchor. The suture is cinched between the cinch lock and the cinch anchor.

The method may position the cinch into a working channel of an endoscope. In various embodiments, the suture capturing portion is extended out of the working channel of the endoscope.

The method may deploy the cinch anchor within a patient by pressing the handle to overcome a threshold deployment force. The method may also disengage the suture capturing portion from the cinch lock by pulling on the handle to overcome a threshold disengagement force. The cinch may be coupled with a delivery shaft of a hand-held cinching device. The delivery shaft may be positioned in an accessory port of the endoscope. The accessory port may lead to a working channel inside the insertion tube. The suture capturing portion may be rotatable relative to the lumen and/or the insertion tube (e.g., using the handle).

The suture capturing portion may include a snare. In various embodiments, the suture capturing portion may be flexible. In various embodiments, the suture capturing portion may expand after or as it is extended from delivery housing and/or the anchor. In various embodiments, the suture capturing portion defines an opening that is larger than the diameter of the lumen. This advantageously allows the snare/hook to capture the suture easily. Because of the flexibility, the snare/hook (capturing portion) can be retracted into the delivery catheter and anchor housing. To that end, the suture capturing portion may be formed from a wire. The wire may be formed from stainless steel, nitinol, nylon, braided polyester, polypropylene, and/or silk. The suture capturing portion my have a thickness of between about 0.005 inch and about 0.025 inch.

The method may stitch the suture in the patient prior to capturing the suture. The method may also capturing the suture inside the patient body. The suture may be cinched by an interference fit between the cinch anchor and the cinch lock.

In accordance with another embodiment, a cinching system includes an endoscope having an insertion tube. The insertion tube has a plurality of channels. The system further includes a cinching device having a handle movably coupled with a flexible drive wire. The handle is configured to move the drive wire proximally or distally within a working channel of an endoscope. The cinching device includes a suture capturing portion coupled with a distal end of the drive wire. Movement of the drive wire in a distal direction causes movement of the suture capturing portion in a distal direction. The cinching device includes a cinch anchor having a lumen through which the suture capturing portion travels. The cinching device also includes a cinch lock coupled with the suture capturing portion. Movement of the suture capturing portion in a distal direction causes movement of the cinch lock in a distal direction. In a similar manner, movement of the suture capturing portion in a proximal direction causes movement of the cinch lock in a proximal direction. An inner diameter of the lumen is configured to provide an interference fit with the cinch lock when the cinch lock enters the lumen.

In various embodiments, the cinch lock is disengageably coupled with the suture capturing portion. The cinch anchor may also be disengageably coupled with a delivery housing.

Among other things, the system may include a suture. The suture may be stitched in a patient (e.g., before the suture capturing portion captures the suture). The cinch anchor may also have a fastening portion configured to couple the cinch anchor with a delivery housing.

In accordance with another embodiment, a cinching device includes a delivery housing configured to fit within a working channel (e.g., of an endoscope). A cinch anchor is coupled with the delivery housing. The cinch anchor has a lumen extending from a proximal end to a distal end. A suture capturing portion is movably positioned in the lumen. The suture capturing portion is configured to capture a suture. A cinch lock is coupled with the suture capturing portion. The cinch lock is configured to provide an interference fit with an inner diameter formed by the lumen when the cinch lock enters the lumen.

Among other things, the device may include a user-manipulated drive wire coupled with the suture capturing portion. In various embodiments, the suture capturing portion is flexible. The suture capturing portion may include a snare and/or a wire.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 8A schematically shows a cross-sectional view of the distal end of the cinch deployment system in accordance with illustrative embodiments of the invention.

FIG. 8B schematically shows the cross-sectional view of FIG. 8A after the cinch lock is disengaged from the capture portion.

FIGS. 11-14 schematically show a process of capturing and locking the suture to the anchor using the cinches shown in FIGS. 10A-10D, respectively.

FIG. 15A-15G schematically show an alternative embodiment of the suture capturing portion in accordance with illustrative embodiments of the invention.

It should be noted that the foregoing figures and the elements depicted therein is are not necessarily drawn to consistent scale or to any scale. Unless the context otherwise suggests, like elements are indicated by like numerals. The drawings are primarily for illustrative purposes and are not intended to limit the scope of the inventive subject matter described herein.

DESCRIPTION OF ILLUSTRATIVE EMBODIMENTS

In illustrative embodiments, an endoscope has a flexible insertion tube with a working channel through which a cinch extends to capture and cinch a suture. To that end, a cinching device is configured to deliver and deploy the cinch. The cinch deployment system includes a delivery housing coupled with a cinch anchor. The cinch anchor has a central lumen extending therethrough. A snare (or other hooked wire) extends out of the lumen of the anchor and captures one or more free ends of the suture. When the snare is retracted into the lumen of the anchor, a locking mechanism of the snare secures the suture to the anchor. The locking mechanism may then be disengaged from the snare, and the anchor may be disengaged from the delivery device and deployed within a patient. Accordingly, the anchor and the locking device may be used to cinch the sutures and the anchor may be left in the patient's body. Details of illustrative embodiments are discussed below.

In the currently available flexible endoscopy cinching devices known to the inventors, the suture is loaded into the cinch outside the patient's body. Such devices often utilize a suture threader to thread the suture into a cinch, enabling the cinch to advance through a working channel of the endoscope. In contrast, illustrative embodiments capture the suture inside the patient's body at the site of therapy (also referred to as the tissue site or operation site), advantageously allowing more flexibility to the medical practitioner with the usage of tools that do not pre-load the suture.

Figure 1:
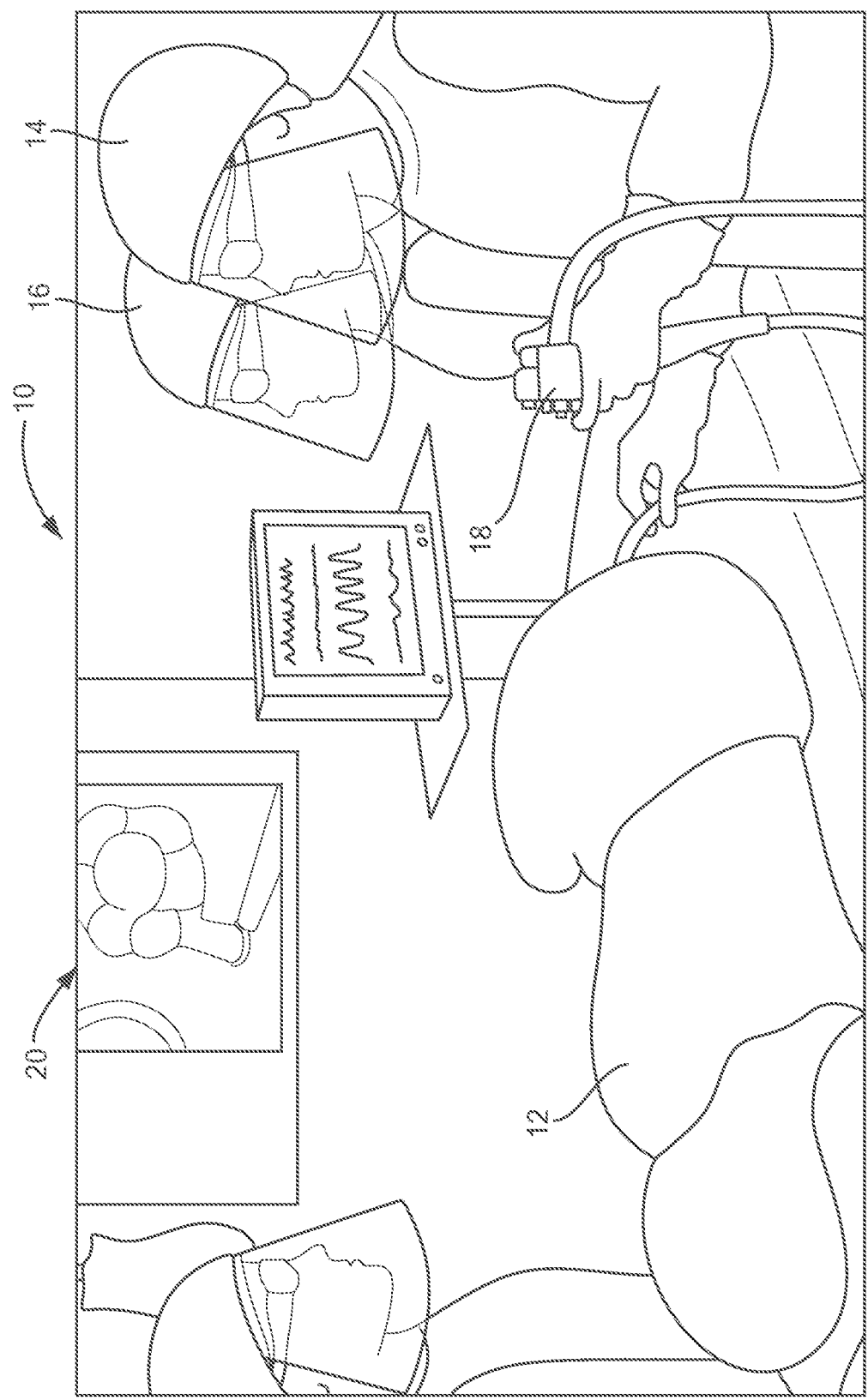
FIG. 1 schematically shows a patient lying on a table in a hospital environment in accordance with illustrative embodiments of the invention.

FIG. 1 schematically shows a patient 12 lying on a surgical table or examination table in a hospital environment 10 in accordance with illustrative embodiments of the invention. The environment 10 may be, for example, within an is endoscopy unit of the hospital. The endoscopy unit may include medical practitioners 14 (e.g., gastroenterologists or surgeons), trained nurses 16, and a variety of medical devices. For example, the medical devices may include an endoscope 18, a video display 20, and other equipment. Procedures performed within the endoscopy unit may include gastrointestinal endoscopy (such as gastroscopy, colonoscopy, ERCP, and endoscopic ultrasound), bronchoscopy, cystoscopy, or other more specialized procedures.

Figure 2A:
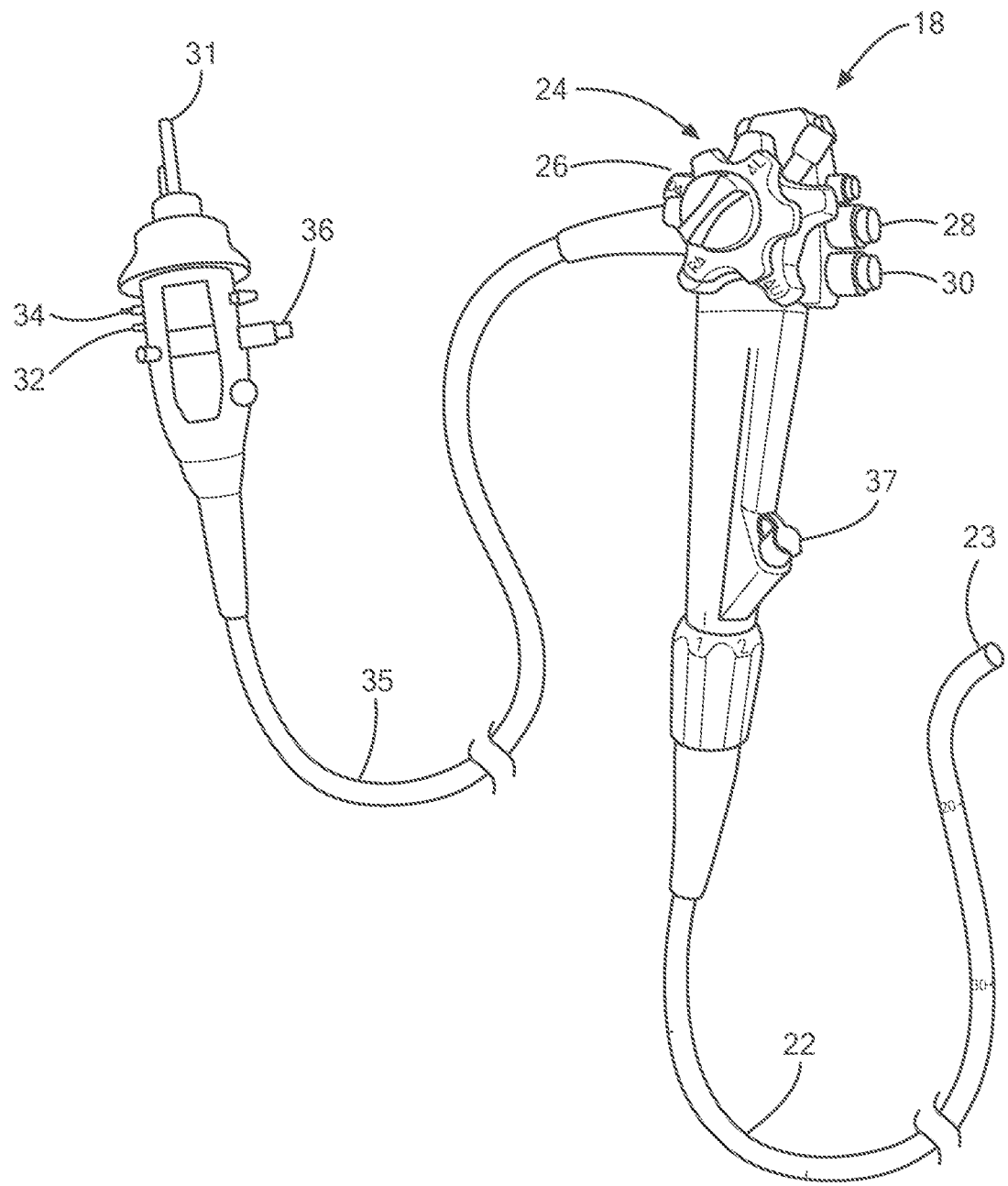
FIG. 2A schematically shows an endoscope in accordance with illustrative embodiments of the invention.
Figure 2B:
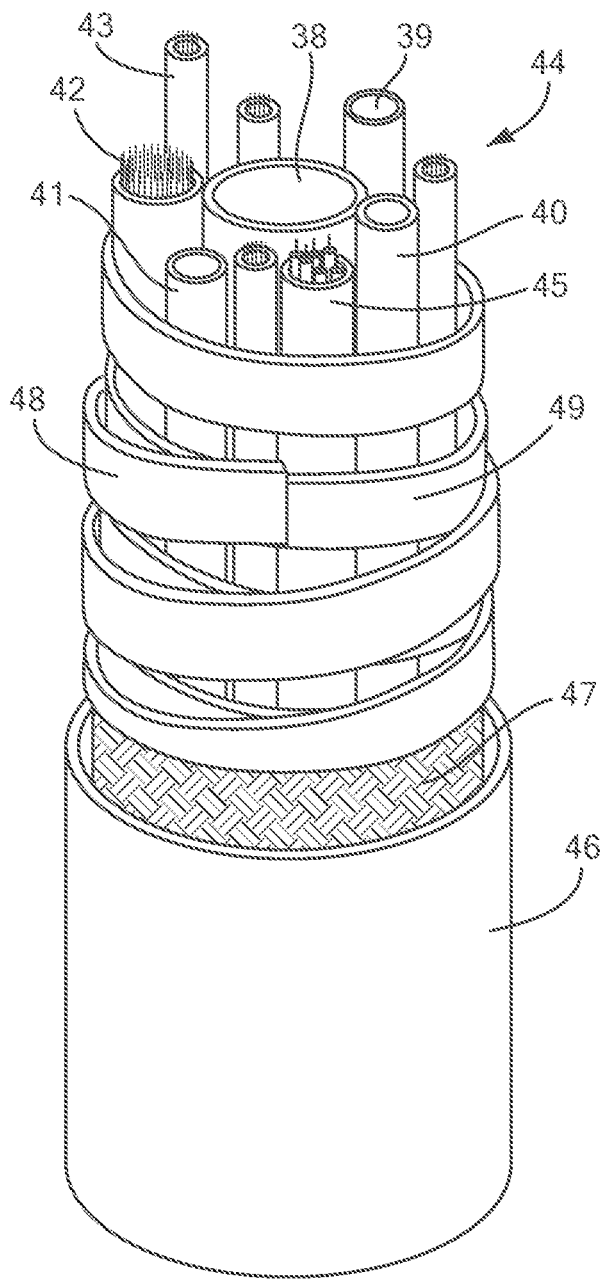
FIG. 2B schematically shows a partially exposed view of the insertion tube in accordance with illustrative embodiments.
Figure 2C:
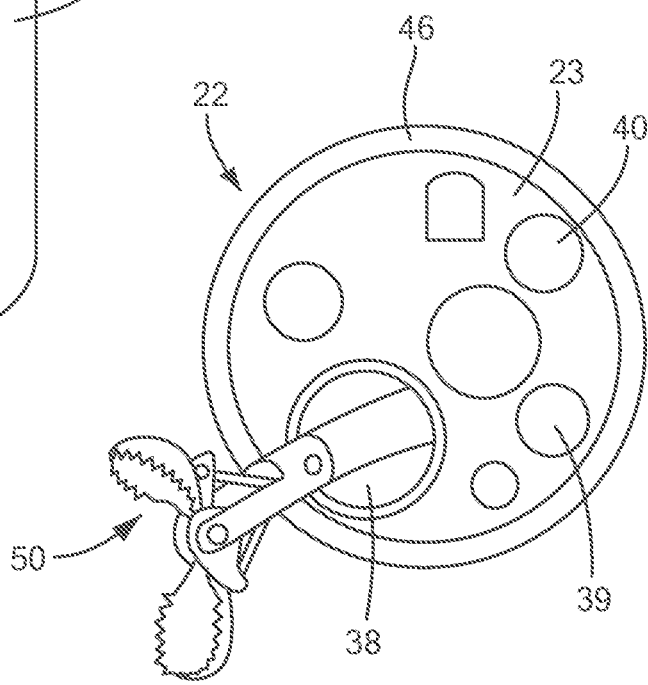
FIG. 2C schematically shows the distal end of the insertion tube in accordance with illustrative embodiments of the invention.

FIGS. 2A-2C schematically show an endoscope 18 in accordance with illustrative embodiments of the invention. As known by those in the art, flexible endoscopes 18 (e.g., colonoscope, gastroscope) are positioned into the body of the patient 12 through the body's natural orifices (e.g., mouth, anus). To that end, the endoscope 18 has a long and flexible insertion tube 22 that is adjustable to the natural pathways within the body. Furthermore, the endoscope 18 has a number of channels running through the insertion tube 22. One of these channels is a working channel, through which tools may be advanced to a distal end 23 of the insertion tube 22.

The endoscope 18 may be contrasted with other devices such as laparoscopes, which are not inserted into the patient's 12 natural orifices. Instead, laparoscopes are inserted into one of the access holes made in the patient 12 during a laparoscopic procedure. Usually, three access holes are made for laparoscopy procedures, one for the rigid scope, and two ports for the tools such as forceps, scissor, suture, etc. Laparoscopes have a non-flexible, rigid, and short insertion tube that is sent through one of the access holes into the body. Generally, laparoscopes do not have a working channel for running tools therethrough. In contrast, the insertion tube 22 of the endoscope 18 (colonoscope, gastroscope) is flexible to travel through the body's natural orifices and has a working channel. Various embodiments may be used with a variety of scopes, such as laparoscopes. However, preferred embodiments are used with a flexible insertion tube 22.

The endoscope 18 has a control section 26 to help guide the insertion tube 22 through the patient's 12 bodily pathways (e.g., the winding GI tract). To that end, the endoscope 18 includes control dials 26 that allow control of the position and orientation of the insertion tube 22 (e.g., bending of the distal end 23 up or down, and right or left). Like many endoscopes, the endoscope 18 may have a plurality of imaging controls, such as an image freeze button and image capture button. There may also be control chromoendoscopy buttons that may change the color of the video in the display 20. The control section 24 may also include a suction button 28 and an air/water button 30. The endoscope 18 may be connected to a light supply via a light guide 31, an air supply via an air supply connector 32, a water supply via a water supply connector 34, and a suction supply via a suction connector 36. Thus, light, air, water, and/or suction, may be delivered through the umbilical cord 35 to the distal end 23 of the insertion tube 22 through the various aforementioned channels.

Water, air, suction, and other functions may selectively be applied at the distal end 23 via separate channels within the insertion tube 22. For example, the user may press the water button 30 to selectively spray water out of the distal end 23. To that end, water is pulled from an external water supply through the water supply connector 34, passes through an umbilical cord 35 of the endoscope 18, and then goes down the insertion tube 22 and out of the distal end 23. A similar process is followed for other functions, including light and suction. Each of these functions may have a dedicated channel within the endoscope 18.

FIG. 2B schematically shows a partially exposed view of the insertion tube 22 in accordance with illustrative embodiments. The insertion tube 22 has a plurality of channels 38-41 and wires 42-45 within the insertion tube 22 that are configured to provide various utility to the endoscope 18. For example, the insertion tube 22 includes the biopsy channel 38, an air channel 39, a water channel 40, and a water jet channel 41. The insertion tube 22 may also include light guide fibers 42, a wire for adjustable stiffness 43, angulation wires 44, and CCD signal wires 45, among other things. These channels 38-41 and wires 42-45 are within a housing of the insertion tube 22. The housing of the insertion tube 22 may include an out outer polymer top coat and base layer 46. Underneath the polymer top coat 46 may be a stainless steel wire mesh 47, along with an outer spiral metal band 48 an inner spiral metal bands 49.

FIG. 2C schematically shows the distal end 23 of the insertion tube 22 with a tool 50 extending out of the working channel 38 in accordance with illustrative embodiments of the invention. The tool 50 may be positioned in the working channel 38 by passing through an accessory port 37 (shown in FIG. 2A). For example, FIG. 2C schematically shows a biopsy forceps 50 extending out of the working channel 38. Various embodiments use a cinching delivery device 54 to deliver a cinch via the working channel 38.

Figure 3:
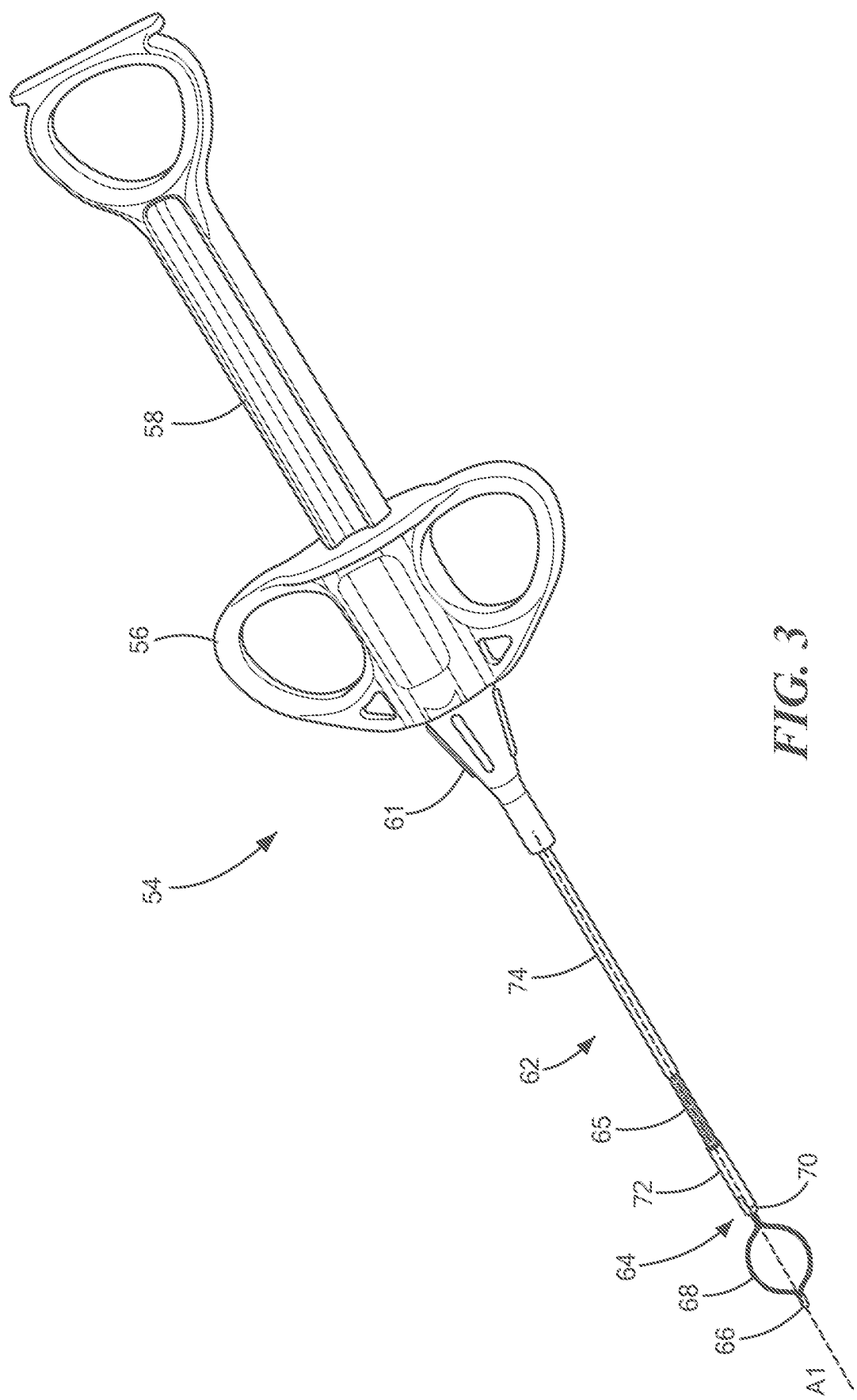
FIG. 3 schematically shows a cinching device in accordance with illustrative embodiments.

FIG. 3 schematically shows a cinching device 54 in accordance with illustrative embodiments. The cinching device 54 includes a handle slider 56 with openings configured to receive the practitioner's 14 thumb fingers. During use, the handle slider 56 slides along a handle frame 58. Movement of the handle slider 56 relative to the handle frame 58 causes a drive wire inside delivery shaft 74 to move proximally or distally along the delivery shaft 74. In various embodiments, the drive wire 60 (also referred to as a pull wire 60) may be movable in an axial direction (e.g., along A1) within a delivery shaft 74. The drive wire 60 may be a long pull wire such as a Bowden cable, which is inside a Bowden coil 65 for support. The Bowden coil (or spring guide) supports the pull wire 60. The pull wire 60 has a small diameter and generally does not have a structural support on its own. In various embodiments, the Bowden coil 65 provides the structural support to the pull wire 60 (while going through working channel, etc.). It should be understood that although A1 is shown as a straight axis, that in various embodiments, the delivery shaft is configured to bend and/or twist in a manner similar to the insertion tube 22. Therefore, moving along the axis A1 may not be straight line axial movement.

The suture cinching device 54 includes a cinch deployment system 62 configured to deploy the cinch 64. The cinch 64 is configured to cinch one or more sutures that have been threaded within the patient 12 (e.g., within the patient's GI tract). The cinch 64 includes a cinch lock 66, a suture capturing portion 68 (e.g., a snare or a wire), and a cinch anchor 70. The cinch anchor 70 sits within a delivery housing 72 at a distal end of the delivery shaft 74. In some embodiments, the first anchor fastener 83 is configured to couple the anchor 70 to the delivery housing 72. In some embodiments, the cinch anchor 70 includes an anchor fastener 83 (see FIG. 6A) configured to couple the cinch anchor 70 with the delivery housing 72. To that end, the delivery housing 72 may include a counterpart anchor fastener in the delivery housing 72. In some embodiments, the first anchor fastener 83 is configured to permanently couple to a second anchor fastener in the delivery housing 72. In some embodiments, the first anchor fastener 83 is configured to removably couple with the counterpart anchor fastener 113 in the delivery housing 72. For example, the first anchor fastener 83 may include a circular protrusion and the second anchor fastener may be a cavity configured to receive the protrusion. The circular protrusion may snap into the cavity by deforming, or by deforming a portion of the circumference of the cavity. Alternatively, the first anchor fastener 83, and/or the counterpart second anchor fastener may include a snap, a hook, a weld, an adhesive, a thread, a pin, or any combination thereof. However, in some embodiments, the cinch anchor 70 and the delivery housing 72 may be formed as a single component.

Figure 4:
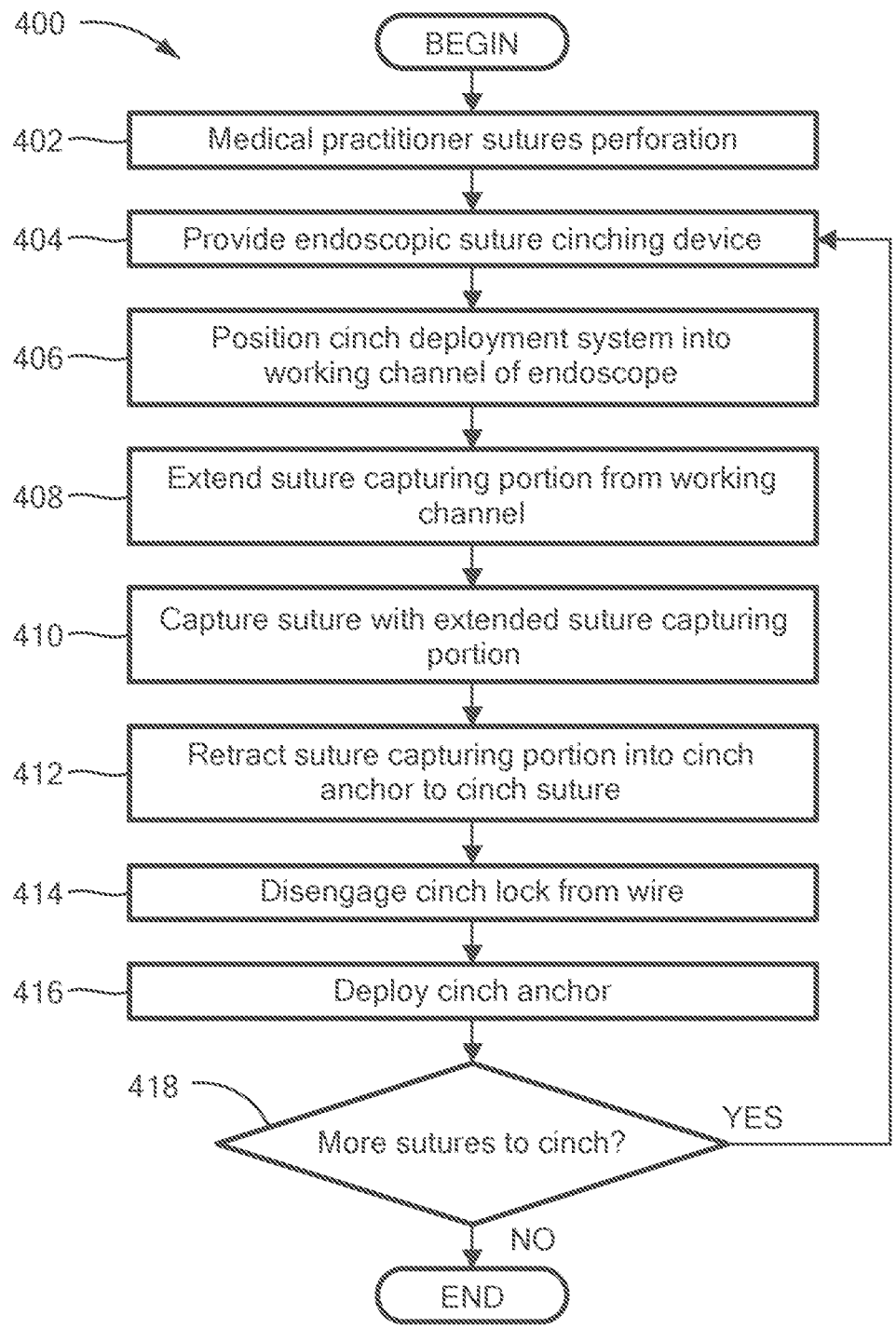
FIG. 4 shows a process of cinching a suture in accordance with illustrative embodiments of the invention.

FIG. 4 shows a process 400 of cinching a suture in accordance with illustrative embodiments of the invention. It should be noted that this process is simplified from a longer process that normally would be used to cinch the suture. Accordingly, the process 400 of cinching the suture likely has many steps that those skilled in the art likely would use. In addition, some of the steps may be performed in a different order than that shown. Additionally, or alternatively, some of the steps may be performed at the same time. Those skilled in the art therefore can modify the process 400 as appropriate.

The process 400 begins at step 402, where the medical practitioner 14 sutures a perforation inside of the patient 12. The process of suturing a perforation is known in the art and therefore is not described in great detail. In general, the process involves grasping tissue near the perforation (e.g., using a tissue grasping tool 50), retracting the tissue, driving a needle coupled to the suture through the tissue, and repeating the stitches as desired. Thus, in the above described example, the suture has two ends: a first end coupled with the needle, and a second free end. Various embodiments may cinch the free end of the suture and/or the first end coupled with the needle together or separately. In some other embodiments, the suture is coupled to a needle that is part of a needle assembly (e.g., that passes through the tissue and grips the tissue). The suture may thus be considered to have a single free end, and a second anchored end. Accordingly, some embodiments may cinch just a single end of the suture. However, some other embodiments may cinch a plurality of locations along the suture (e.g., both ends of one or more sutures). The suture may be formed of any materials commonly used for surgical suture, such as stainless steel, nitinol, nylon, braided polyester, polypropylene, and/or silk.

The process proceeds to step 404, which provides the endoscopic suture cinching device 54. The device 54 may be provided to the medical practitioner 14 during and/or after a medical procedure, such as a polypectomy. During the medical procedure, the medical practitioner 14 may take a biopsy from the patient 12 by using the biopsy tool 50 (e.g., biopsy forceps) to remove a polyp. The biopsy tool 50 may be placed within the working channel 38 of the endoscope 18. The medical practitioner 14 may then use any suturing tool to suture the perforation. In various embodiments, the suturing tool may be attached to the outside of the distal end 23 of the insertion tube 22. Various embodiments of the endoscope 18 may include one or more working channels 38.

Illustrative embodiments work with a variety of sutures and/or endoscopic suturing devices. For example, illustrative embodiments advantageously do not require pre-loading the suture into the suture cinching device 54, or passing the suture through the accessory port 37 of the endoscope 18. Advantageously, the suture cinching device 54 may be used to cinch a suture that was previously applied to the patient 12 (e.g., to a perforation) using an integrated or separate stitching tool.

Figure 5B:
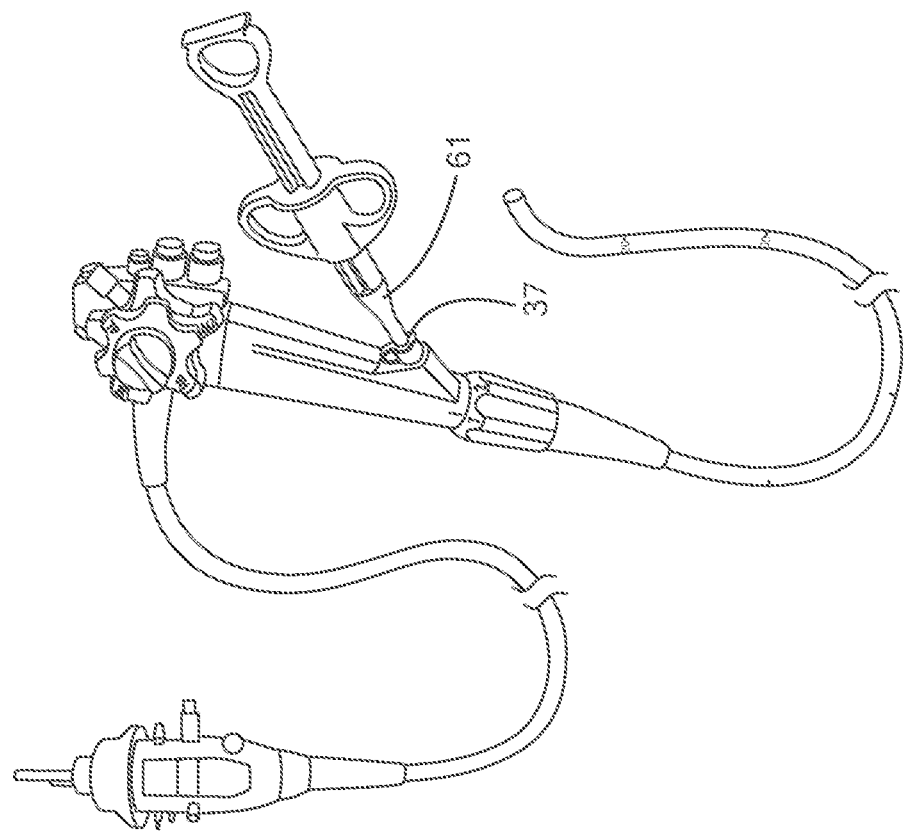
FIGS. 5A-5B schematically show the delivery shaft advancing into the access port suture in accordance with illustrative embodiments of the invention.
Figure 5A:
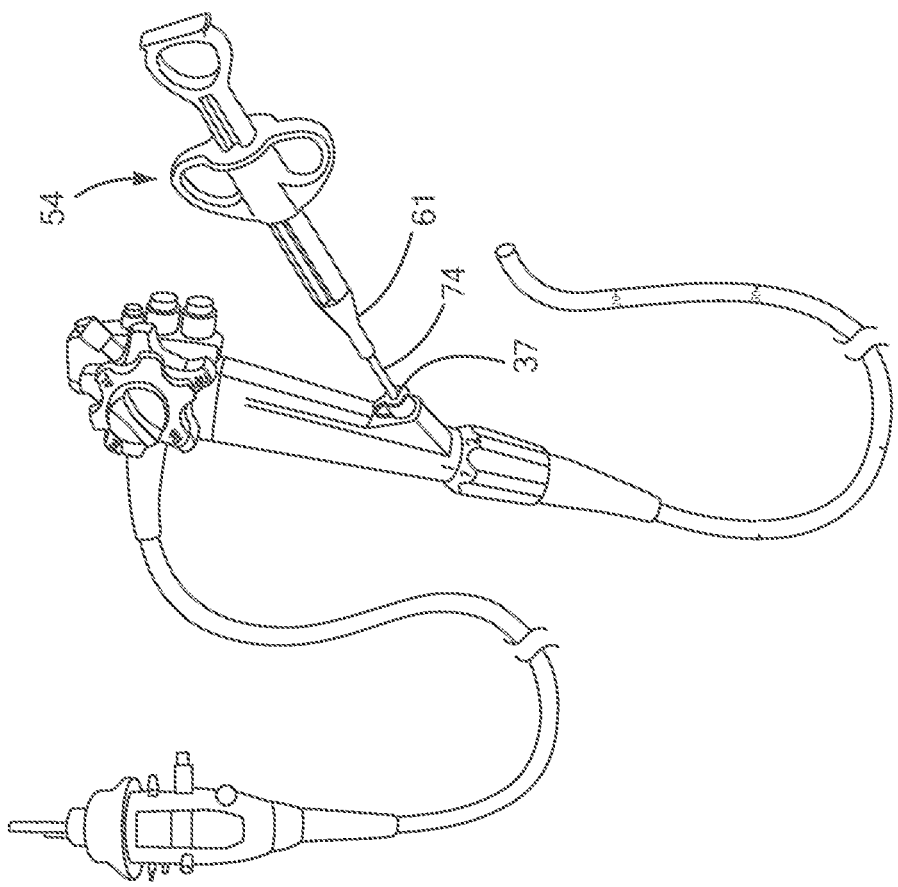

The process proceeds to step 406, which positions the cinch deployment system 62 into the working channel 38 of the endoscope 18. To that end, a distal end of the delivery shaft 74 may be positioned with the access port 37 of the endoscope 18. FIGS. 5A-5B schematically show the delivery shaft 74 advancing into the access port 37. The delivery shaft 74 may be driven into the access port 37. As shown, the delivery shaft 74 may advantageously flex in a manner similar to the insertion tube 22. It should be further understood that the endoscope 18 and cinching device 54 are not necessarily drawn to scale. However, various components are shown here for purposes of discussion.

Figure 5C:
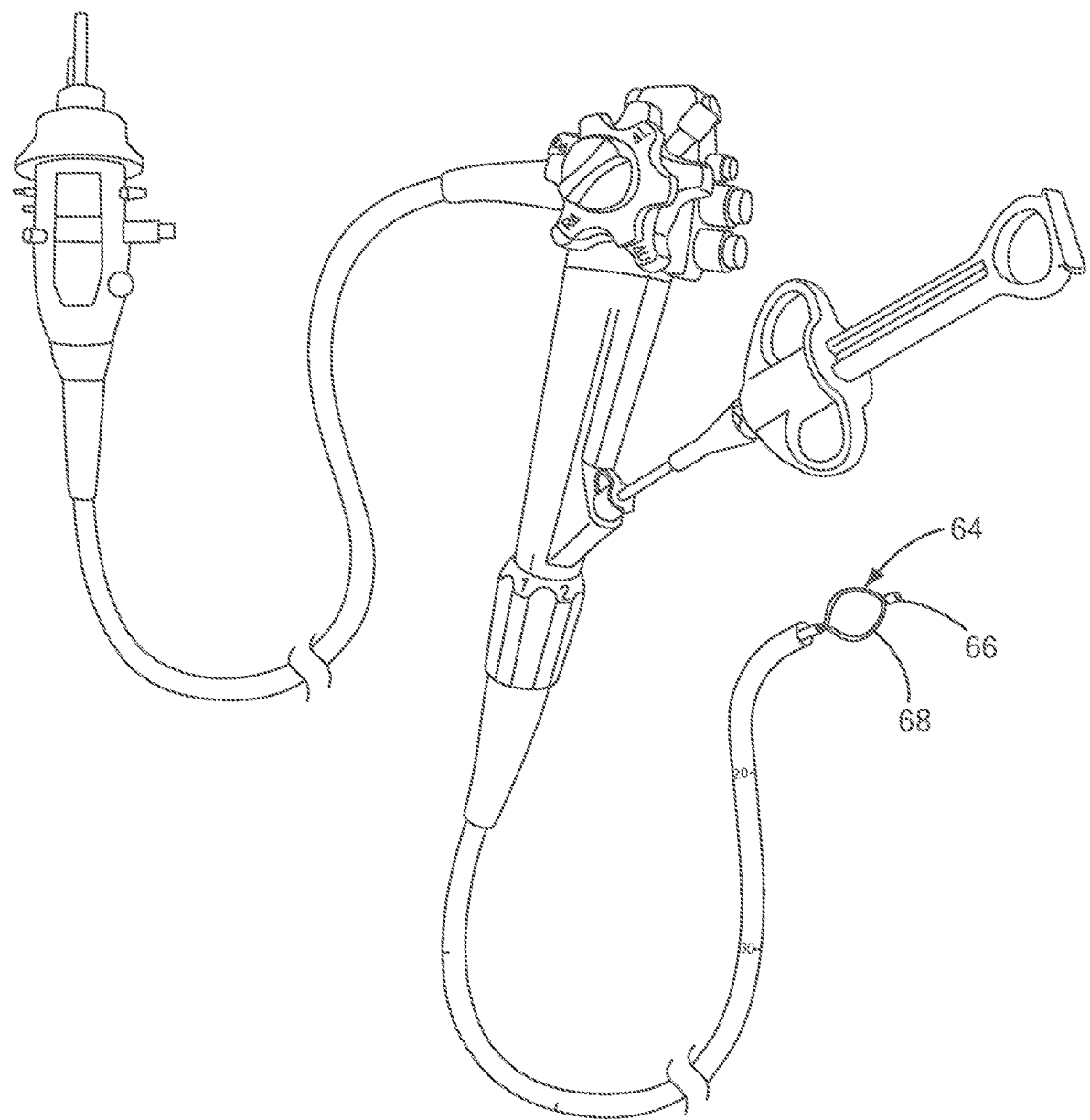
FIG. 5C schematically shows the suture capturing portion extended from the working channel in accordance with illustrative embodiments of the invention.

At step 408, the process extends a suture capturing portion 68 from the working channel of the endoscope 18. Based on physician's 14 technique and also how much space is available in the patient 12 body, the delivery housing 72 can also be fully extended out of the working channel 38, partially outside, or even inside of the working channel 38. FIG. 5C schematically shows the suture capturing portion 68 extended from the working channel 38 in accordance with illustrative embodiments of the invention. In FIG. 5C the suture capturing portion 68 is shown as a snare. However, some embodiments may include a hook and/or other shape configured to capture the suture. In preferred embodiments, the suture capturing portion 68 is flexible. In various embodiments, the suture capturing portion 68 may expand after or as it extends out of the delivery housing 72 and/or anchor 70. In various embodiments, the suture capturing portion 68 defines an opening 79 that is larger than the diameter of the lumen 73. This advantageously allows the snare/hook to capture the suture 78 easily. Because of the flexibility, the snare/hook (capturing portion) can be retracted into the delivery catheter (e.g., delivery housing 72) and/or the anchor 70.

To that end, the suture capturing portion 68 may be formed from a wire. For example, the suture capturing portion 68 may be a thin nitinol or stainless-steel wire. The capturing portion 68 (e.g., the wire) may have a thickness of between about 0.005 inch to about 0.025 inch. Among other shapes, the capturing portion 68 may have a circular, rectangular, square, elliptical, or hexagonal, cross-section. The capturing portion can be formed from, among other things, solid wire, multi-stranded wire, stamped material, injection molded plastic such as PEEK, polycarbonate, polypropylene, and/or ABS. However, the suture capturing portion 68 may take a variety of forms. For example, the suture capturing portion and the suture may be magnetically attractive to one another. Alternatively, the suture capturing portion may have an adhesive configured to grasp the suture.

Figure 6A:
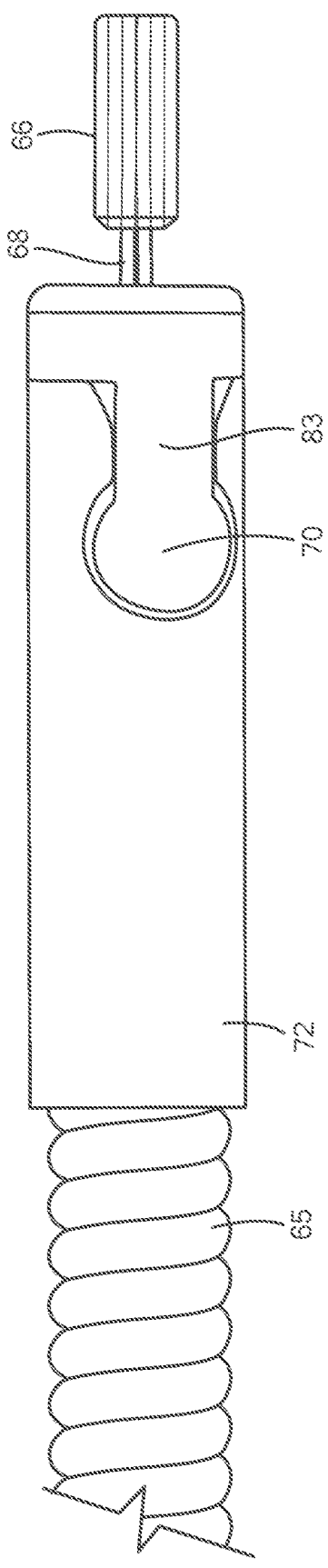
FIG. 6A schematically shows a part of the suture capturing portion beginning to extend from the delivery housing.

In various embodiments, the capturing portion 68 may be formed as a snare or loop that is biased towards an open configuration (e.g., open position shown in FIG. 5C). FIG. 6A schematically shows a part of the suture capturing portion 68 beginning to extend from the delivery housing 72. In this view, the insertion tube 22 is omitted for clarity. However, it should be understood that the delivery housing 72 is positioned within the working channel 38 of the insertion tube 22 (e.g., see FIG. 2C). As shown, when the loop is in the delivery housing 72, the delivery housing 72 presses the loop into the closed position.

Figure 6B:
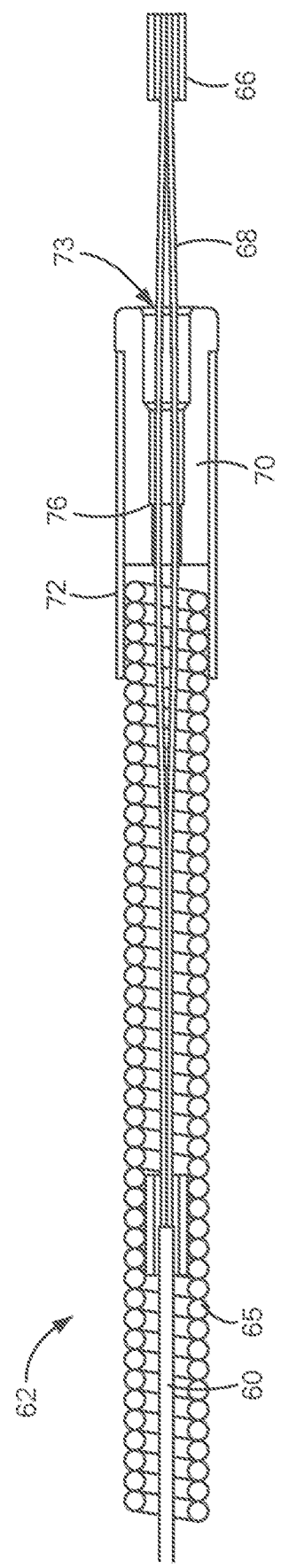
FIG. 6B schematically shows a cross-sectional view of the cinch deployment system in accordance with illustrative embodiments.

FIG. 6B schematically shows a cross-sectional view of the cinch deployment system 62 in accordance with illustrative embodiments. As shown, the suture capturing portion 68 is extended further than shown in FIG. 6A. The cinch anchor 70 has a lumen 73 through which the suturing capturing portion 68 extends. To that end, the suture capturing portion 68 may be extended out of the working channel 38 by the medical practitioner 14 pressing the handle frame 58, which is coupled with a proximal end of the drive wire 60. As the drive wire 60 is pressed, the suture capturing portion 68 is advanced and extended out of the lumen 73 of the anchor 70.

In various embodiments, the suture capturing portion is coupled with the cinch lock 66. The cinch lock 66 is configured to retain the captured suture within the cinch anchor 70. To that end, an inner diameter of the lumen 73 may be configured to provide an interference fit with the cinch lock 66. Specifically, the suture becomes trapped between the cinch lock 66 and the cinch anchor 70 when the suture capturing portion 68 is fully retracted into the cinch anchor 70. The cinch anchor 70 may also have a counterpart shoulder 76 which prevents the cinch lock 66 from being retracted further into the working channel 38, as will be described in more detail later. The cinch lock 66 may have a cross-sectional shape of a rectangle, square, a circle, a triangle, a diamond, or any combination thereof.

Figure 7A:
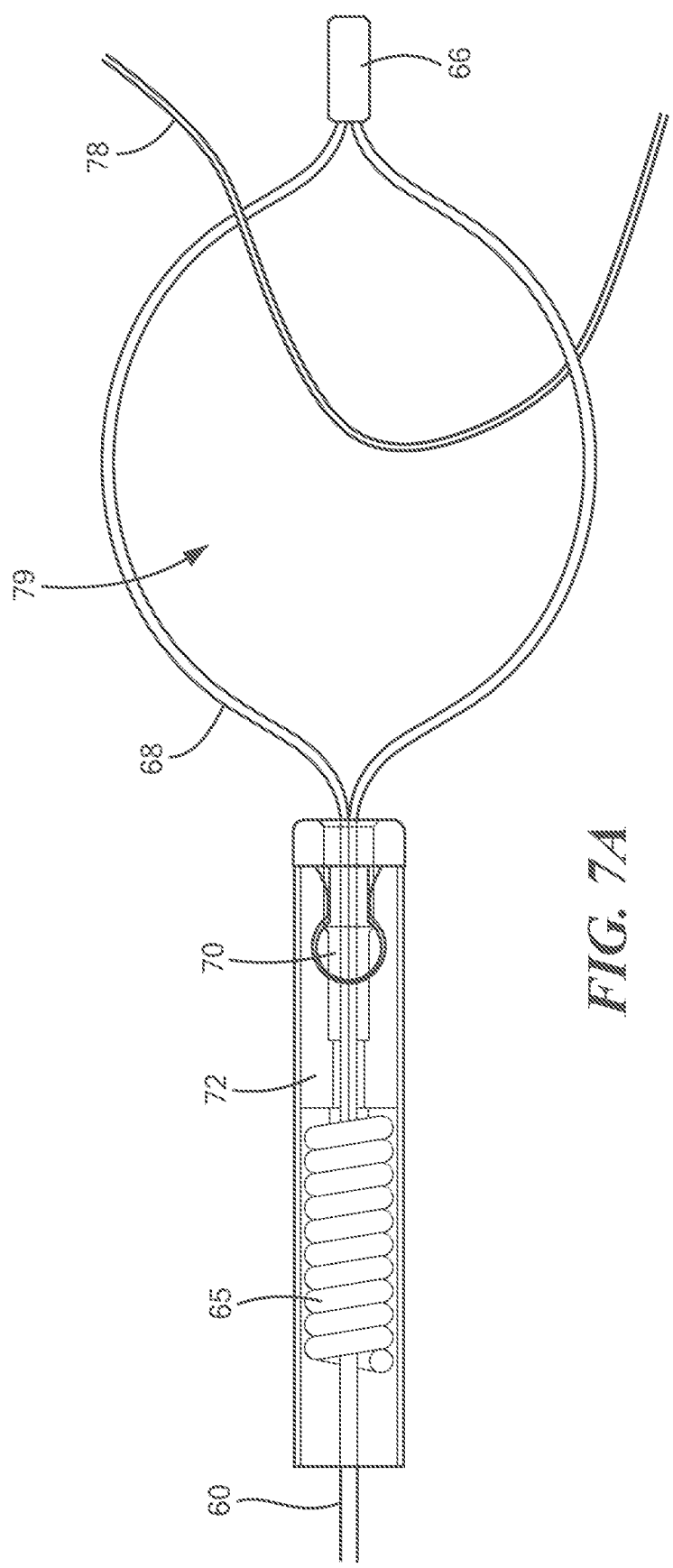
FIG. 7A schematically shows the suture capturing portion capturing the suture in accordance with illustrative embodiments of the invention.

After the suture capturing portion 68 is extended, the suture is captured at step 410. FIG. 7A schematically shows the suture capturing portion 68 capturing the suture 78 in accordance with illustrative embodiments of the invention. The suture 78 may be passed through an opening 79 of the suture capturing portion 68, as shown in FIG. 7A. Alternatively, the suture capturing portion 68 may be positioned over a free end of the suture 78. In some other embodiments, the suture 78 may be hooked, clipped, wound, or otherwise retained the suture capturing portion 68. Furthermore, various embodiments may capture use a tool 50 to assist with capturing the suture 78. For example, a needle, a clamp, and/or a forceps, may be used to help the capturing portion 68 capture the suture 78.

Figure 7B:
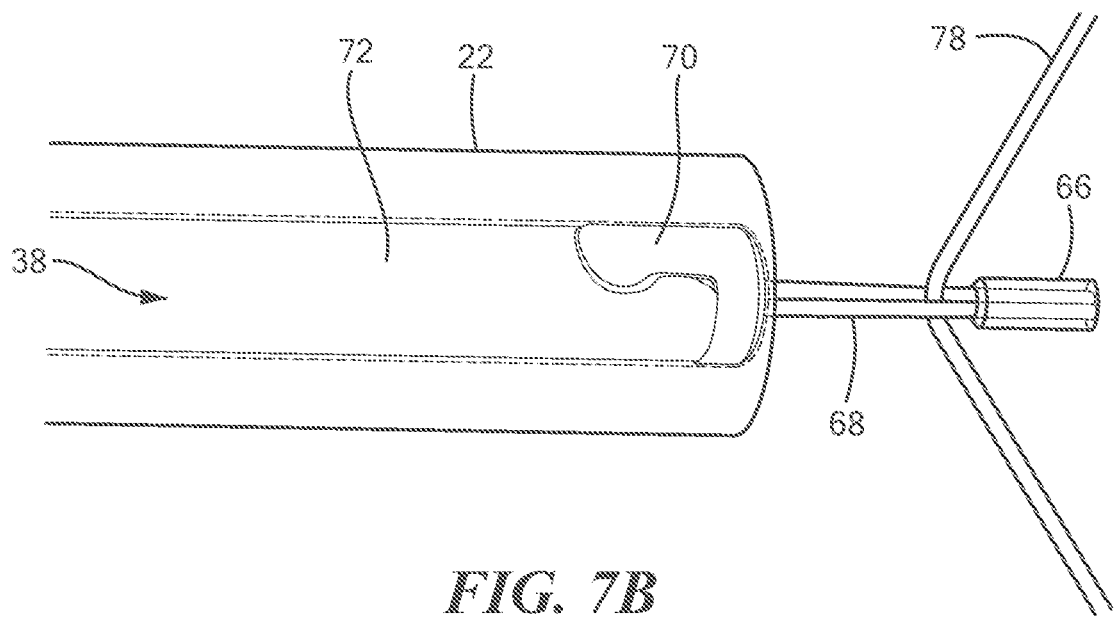
FIGS. 7B-7E schematically show the captured suture being pulled into the working channel of the insertion tube in accordance with illustrative embodiments.
Figure 7C:
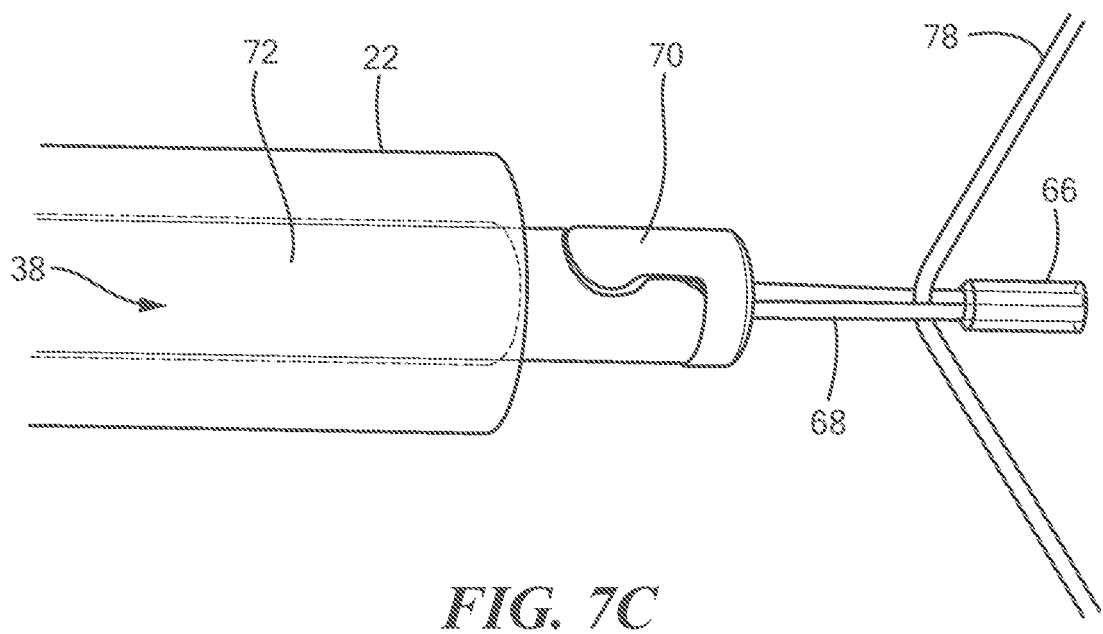
Figure 7D:
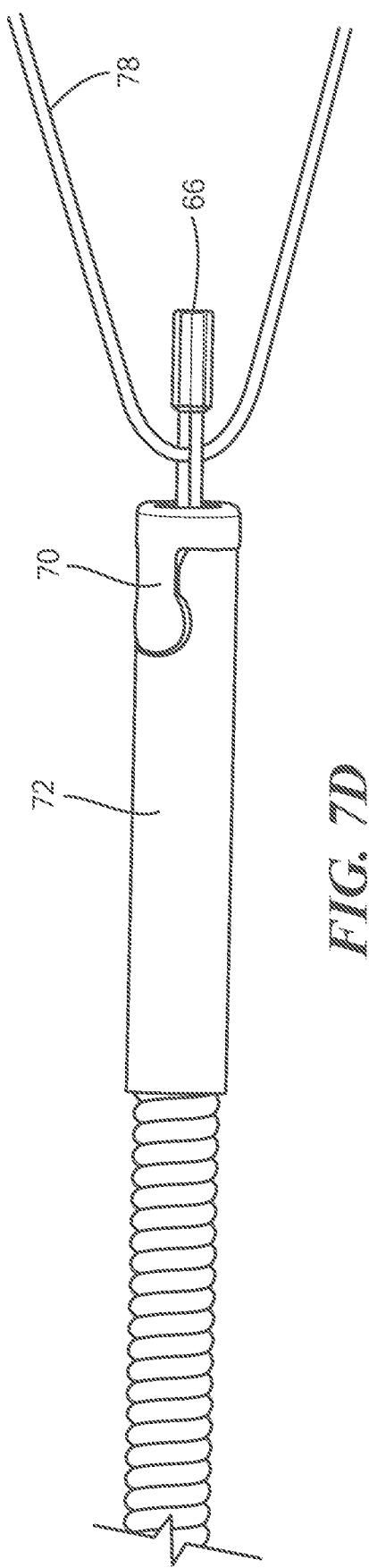
Figure 7E:
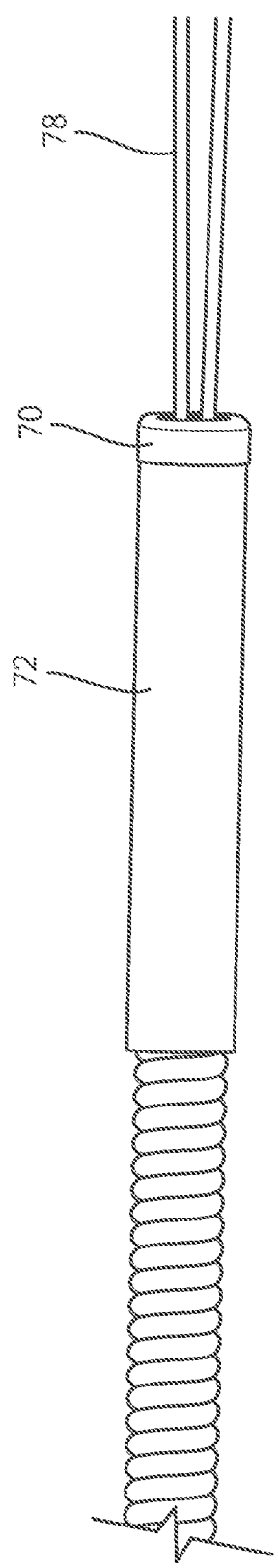

The process then proceeds to step 412, which retracts the suture capturing portion 68 into the cinch anchor 70 to cinch the suture 78. FIGS. 7B-7E schematically show the captured suture 78 being pulled into the anchor 70 in accordance with illustrative embodiments. As shown in FIG. 7B, the delivery housing 72 may be positioned within the working channel 38 (shown in broken lines) of the insertion tube 22. However, as shown in FIG. 7C, the delivery housing 72 may be extended out of the working channel 38. Thus, in some embodiments, the suture 78 may be retracted into the cinch anchor 70 and/or delivery housing 72, which may or may not be inside of or extended from the working channel 38. The medical practitioner 14 pulls the handle frame 58 to retract the drive wire 60. Drive wire 60 is coupled with the suture capturing portion 68, and thus, as the drive wire 60 is retracted, the suture capturing portion 68 is also retracted. Because the suture capturing portion 68 has captured the suture 78, the suture 78 is also pulled towards the delivery housing 72 and the anchor 70. Eventually, as shown in FIG. 7E, the suture 78 is pulled into the anchor 70. Furthermore, the cinch lock 66 is also pulled into the cinch anchor 70. In various embodiments, the suture 78 is tensioned by pulling back the suture 78 or insertion tube 22 and then bringing the delivery housing 72 closer to the tissue at the incision site to ensure that the cinch is tight.

FIG. 8A schematically shows a cross-sectional view of the distal end of the cinch deployment system 62 in accordance with illustrative embodiments of the invention. As shown, the suture capturing portion 68 and the cinch lock 66 have been retracted into the cinch anchor 70. Cinch lock 66 comes to rest against a shoulder 76 formed by the inner diameter of the lumen 73. Additionally, or alternatively, the inner diameter of the lumen may be tapered. The medical practitioner 14 pulls sufficiently tight on the handle frame 58, such that the suture 78 is wedged between the cinch lock 66 and the cinch anchor 70. Accordingly, the suture 78 is cinched by the cinch mechanism.

The process then proceeds to step 414, which disengages the cinch lock 66 from the capture portion 68. FIG. 8B schematically shows the cross-sectional view of FIG. 8A after the cinch lock 66 is disengaged from the capture portion 68. The medical practitioner 14 may pull on the drive wire 60 coupled with the capture portion 68. The capture portion 68 and the cinch lock 66 are configured so that the capture portion 68 uncouples after a threshold amount of force is met. Thus, the suture capturing portion 68 may be removed from the patient 12.

The process then proceeds to step 416, which deploys the cinched suture 78. Specifically, the cinch anchor 70, which is now coupled with the cinch lock 66 and the suture 78 is deployed. The medical practitioner may press the drive wire 60 (before or after uncoupling the suture capturing portion 68 from the drive wire 60) against the cinch anchor 70 and/or the cinch lock 66. In some embodiments, the broken/disengaged capture portion 6 may be positioned between the drive wire 60 and the cinch anchor 70 and/or cinch lock 66. Regardless, illustrative embodiments may consider the drive wire 60 to be "pressing" against the cinch anchor 70 and/or the cinch lock 66 when deploying the cinch anchor 70, even if the broken snare wire 68 is physically between the drive wire 60 and the anchor 70 or lock 66. After a threshold force is met, the cinch anchor 70 is dislodged from the delivery housing 72 and remains in the patient 12.

Figure 9A:
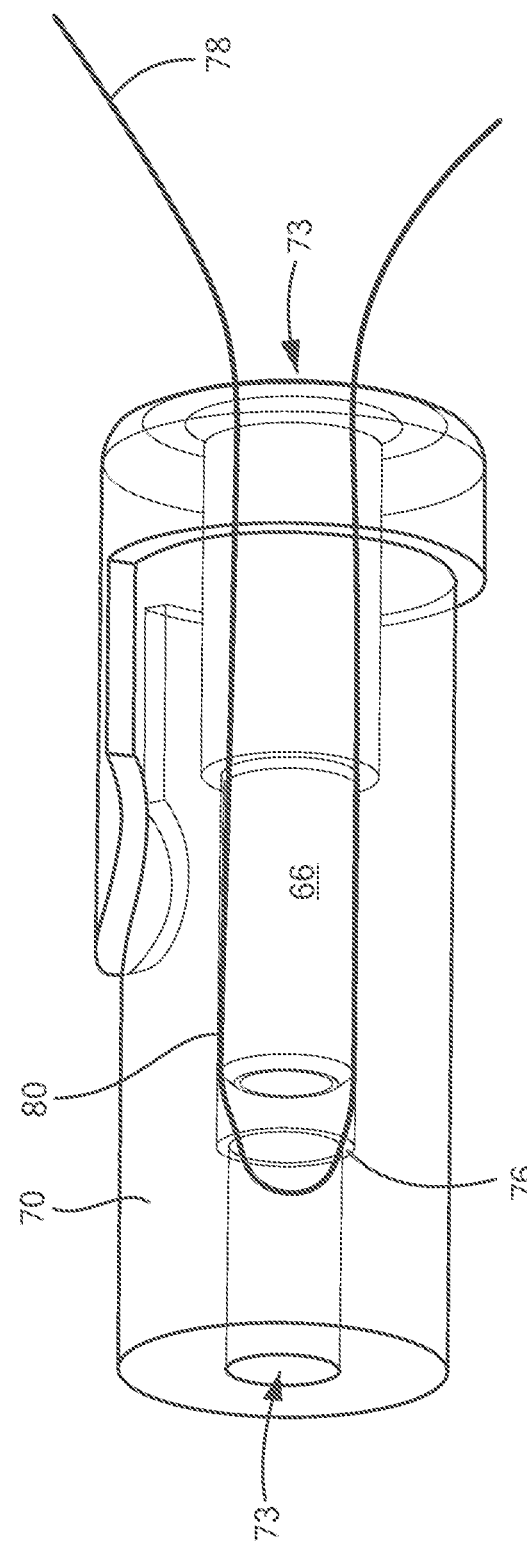
FIG. 9A schematically shows a see-through view of the cinch anchor when the suture is retained by the cinch lock in accordance with illustrative embodiments of the invention.
Figure 9B:
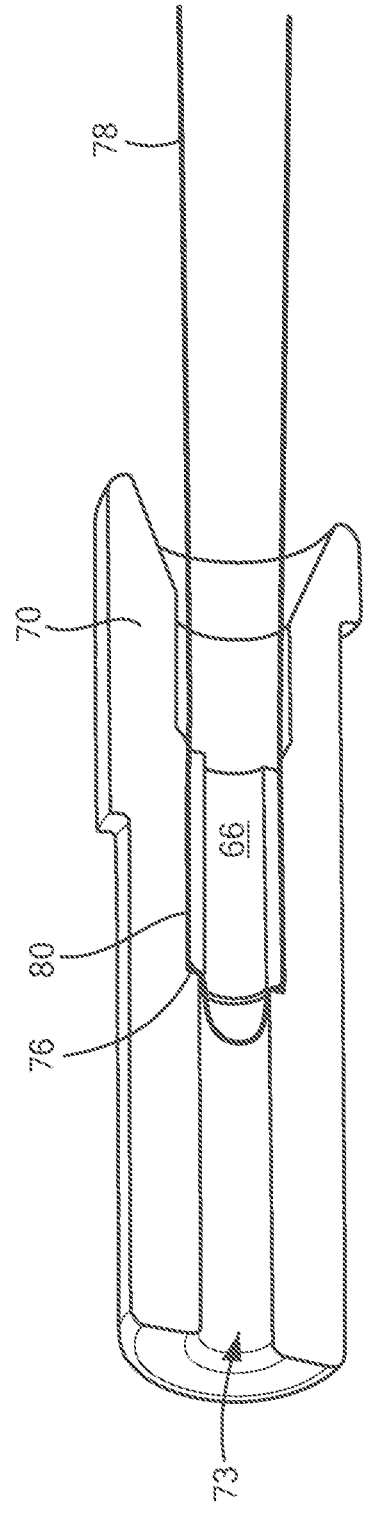
FIG. 9B schematically shows a cross-sectional view of the cinch anchor when the suture is retained by the cinch lock in accordance with illustrative embodiments of the invention.

FIG. 9A schematically shows a see-through view of the cinch anchor 70 when the suture 78 is retained by the cinch lock 66 in accordance with illustrative embodiments of the invention. FIG. 9B schematically shows a cross-sectional view of the cinch anchor 70 when the suture 78 is retained by the cinch lock 66 in accordance with illustrative embodiments of the invention. As shown, an interference fit 80 is created by the cinch lock 66 and the inner diameter of the cinch anchor 70. The interference fit 80 squeezes the suture 78 therein, forming a crimp, and retains the suture 78 to the suture anchor. Accordingly, the suture 78 is now cinched.

The process proceeds to step 418, which asks if there are more sutures to cinch? If yes, then the process returns to step 404, which providing the endoscopic suture cinching device (e.g., with a cinch lock 66 engaged with the suture capturing portion 68). In some embodiments, the suture cinching device is removed from the working channel 38 and an endoscopic scissor may be used to cut the suture 78. The process is then repeated substantially as described above until the suture 78 is cinched. In some embodiments, both ends of the suture 78 are cinched one at a time. In some other embodiments, both ends of the suture 78 may be cinched using a single anchor 70, capturing portion 68, and cinch lock 66. When there are no more sutures 78 to cinch, the process comes to an end.

It should be apparent to one skilled in the art that illustrative embodiments provide a number of advantages to medical practitioners 14 and the patient 12. Specifically, illustrative embodiments advantageously enable cinching the suture 78 at any place along the length of the suture 78 inside the patient 12 body. Illustrative embodiments can cinch the suture 78 as many times as needed. Furthermore, illustrative embodiments advantageously reduce the steps that medical practitioner takes to perform the suturing process. Illustrative embodiments advantageously enable suturing with or without pre-loading the suture 78 into the cinch outside of the patient's body. Furthermore, illustrative embodiments enable the use of a short suture, such that the free end of the suture does not come outside of the patient's body. The suture may be 1 inch to 10 inches, for example. Accordingly, illustrative embodiments may operate with a short or a long because the cinch does not need to be loaded into the cinch at the proximal side of the working channel.

Figure 10A:
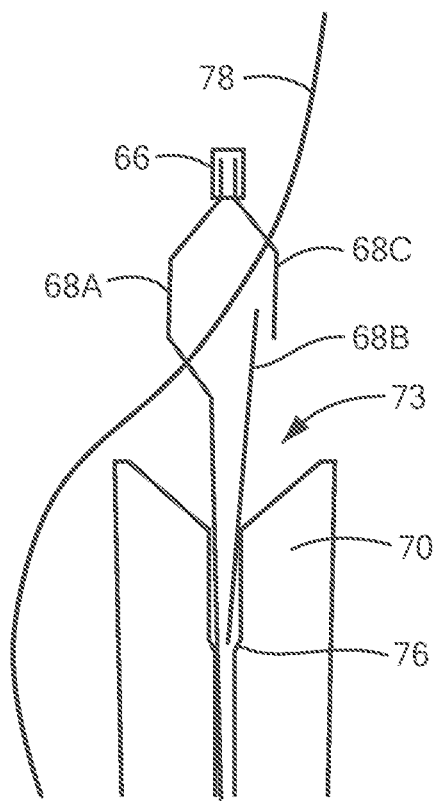
FIGS. 10A-10D schematically show alternative configurations of the cinch in accordance with illustrative embodiments of the invention.

FIGS. 10A-10D schematically show alternative configurations of the cinch 64 in accordance with illustrative embodiments of the invention. For example, FIG. 10A schematically shows an exemplary hook suture capturing portion 68. The hook may be formed from a snare wire 68, and may include a first snare wire 68A, a second snare wire 68B, and a third snare wire 68C. In some embodiments, the third snare wire 68C may be normally closed, but may be biased open by a portion of the anchor 70.

Figure 10B:
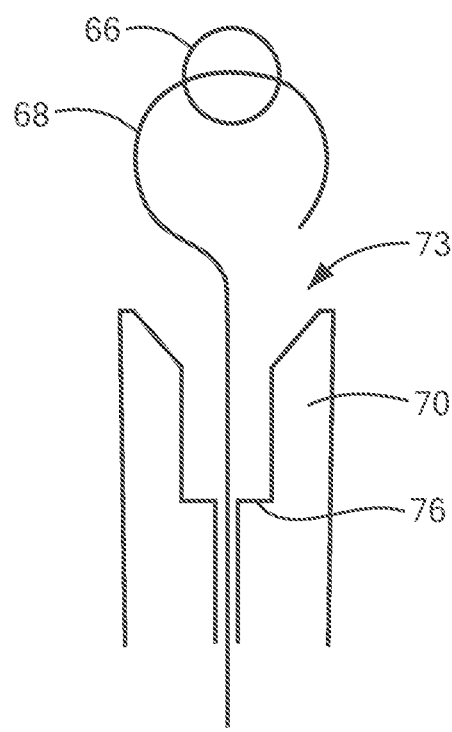
Figure 10C:
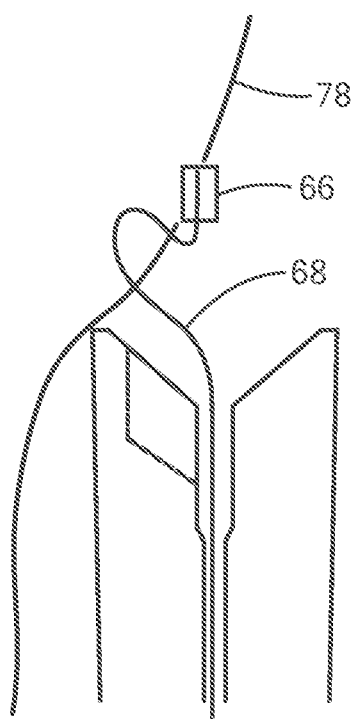
Figure 10D:
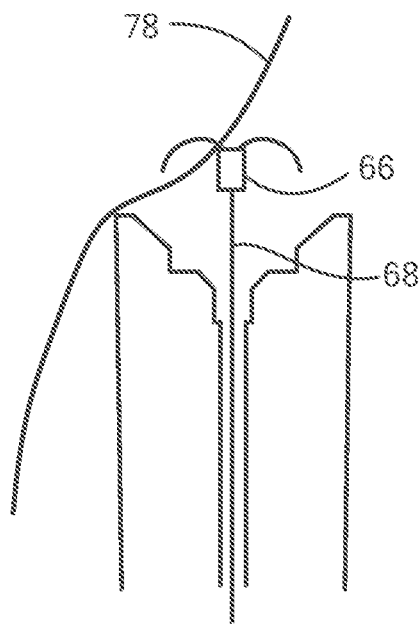
Figure 11:
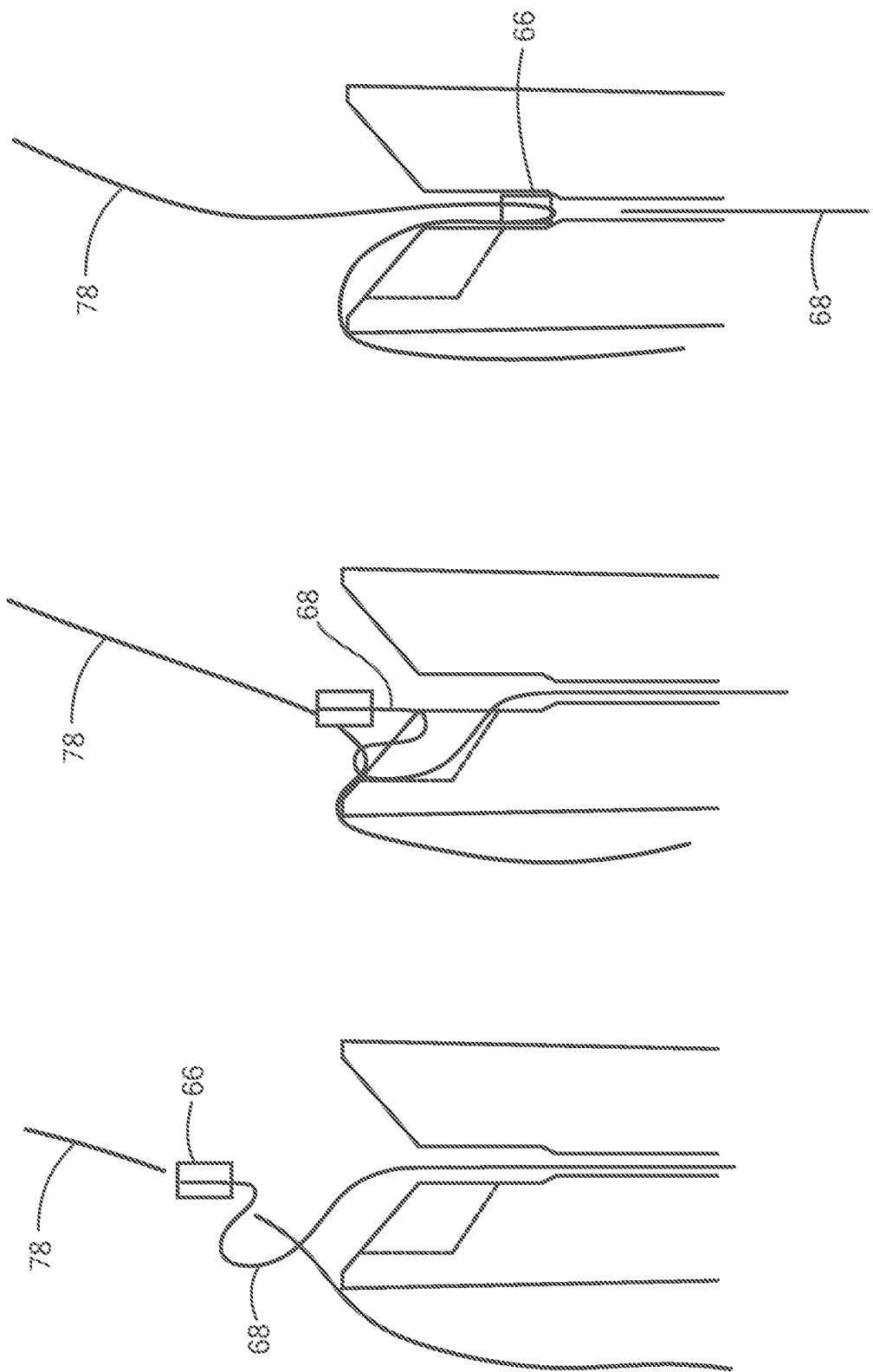

FIG. 10B schematically shows an exemplary ball-snare suture capturing portion 68. The lock 66 is shown as a ball crimp configured to wrap around the suture 78 to capture the suture 78. FIG. 10C schematically shows an exemplary wrap snare suture capturing portion 68. The lock 66 may be a crimp configured to wrap around the suture 78 to capture the suture 78. FIG. 10D schematically shows the suture capturing portion 68 as an exemplary pronged snare 500. The lock 66 is a pronged crimp 130B configured to capture the suture 68. In some embodiments, as shown, the pronged crimp 130B may include 2 prongs. Alternatively, in some embodiments, the pronged crimp 130B may comprise one or more prongs (e.g., 4-prongs separated by 90 degrees of rotation). In some embodiments, the anchor 70 may include a prong crimp cavity 114 to accept at least a portion of the pronged crimp 130B.

Figure 14:
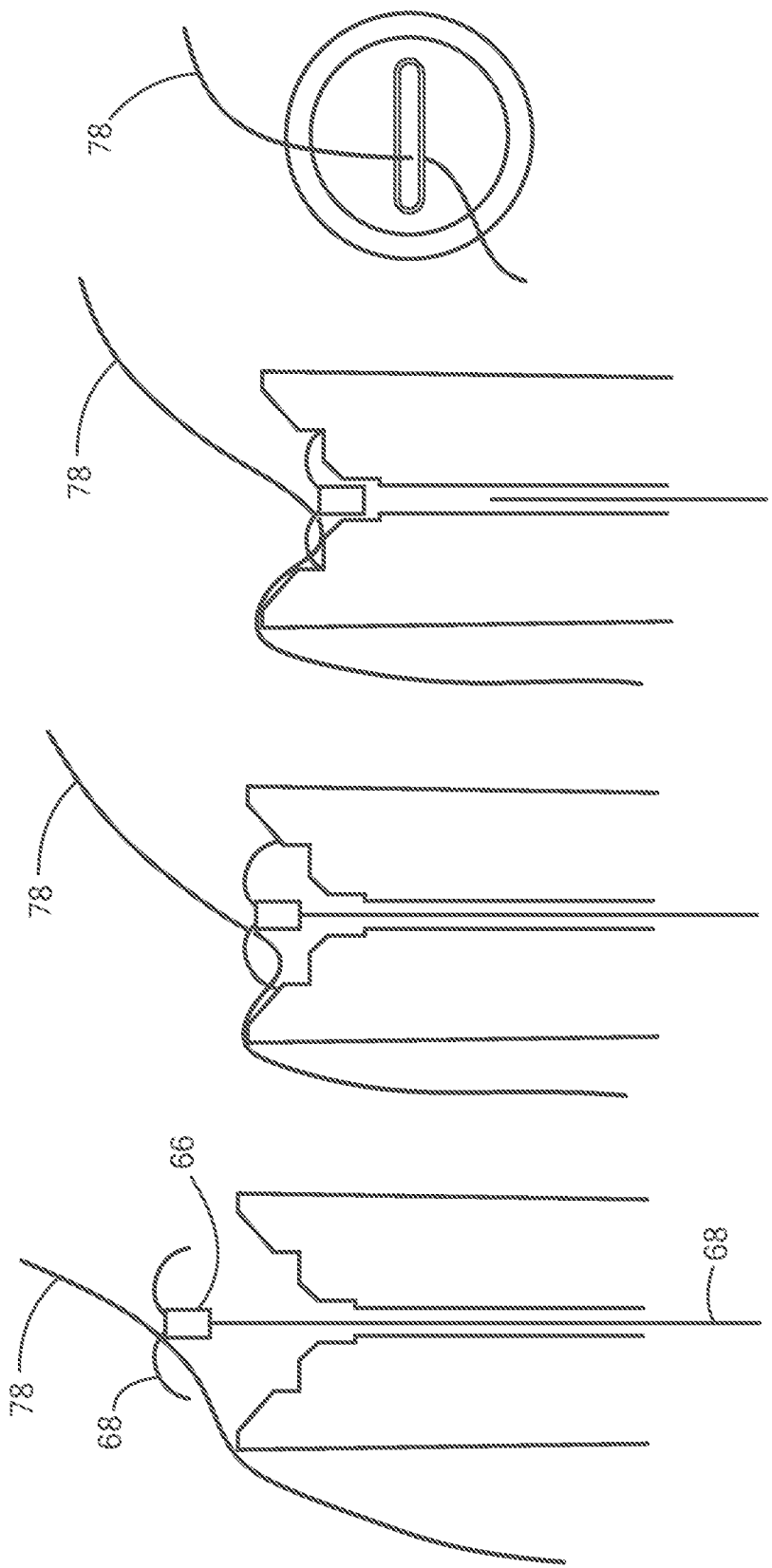

FIGS. 11-14 schematically show a process of capturing and locking the suture 78 to the anchor 70 using the various cinches 64 shown in FIGS. 10A-10D, respectively. As shown in FIG. 14, in some embodiments, the suture capturing portion may be integrated with the cinch lock 66 and/or extend beyond the cinch lock 66.

Figure 15C:
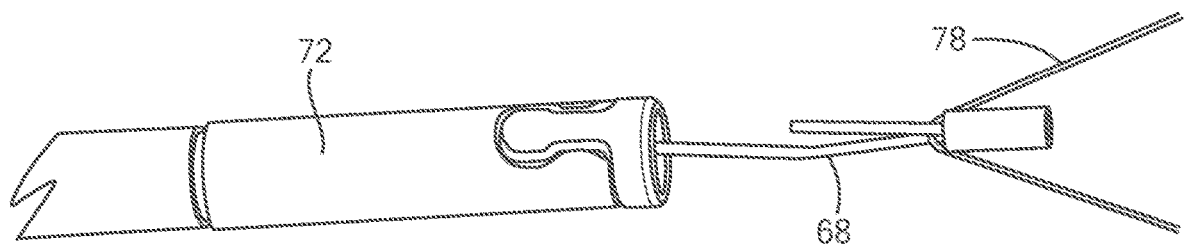

FIG. 15A-15G schematically show an alternative embodiment of the suture capturing portion 68 in accordance with illustrative embodiments of the invention. As shown in FIG. 15A, the suture capturing portion 68 may be an extended and bent wire. In various embodiments, the suture capturing portion 68 may be formed to bias towards a bent configuration when not compressed. The capturing portion 68 may be flexible and/or resilient. While the capturing portion 68 is inside the delivery housing 72, a maximum dimension D3 in a direction perpendicular to the axis A1 is smaller than a diameter D1 of the delivery housing 72 and a diameter D2 of the lumen 73. However, when the capturing portion 68 is outside the delivery housing 72 and/or the anchor 70, the resilient portion 68 returns to its normal bent configuration. This normal configuration may have the maximum dimension D3 greater than the diameter D1 of the housing 72 or the diameter D2 of the lumen 73.

Figure 15D:
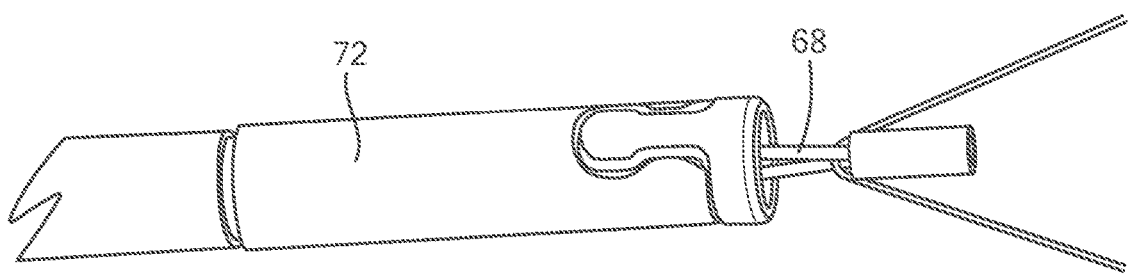
Figure 15E:
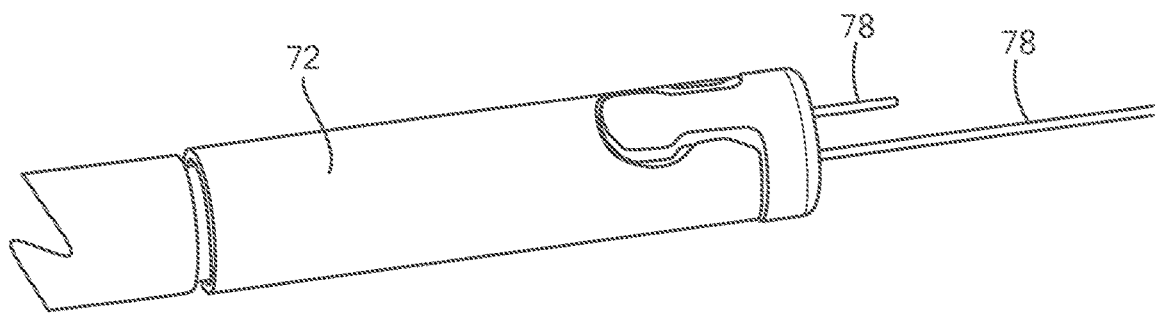

FIG. 15B schematically shows the snare wire 68 fully extended. The wire 68 may form the opening 79 configured to hook the suture 78 and guide it towards the cinch lock 66. FIGS. 15C-15E schematically shows a rotated suture capturing portion 68 with the suture 78 captured being gradually retracted into the housing 72.

Figure 15F:
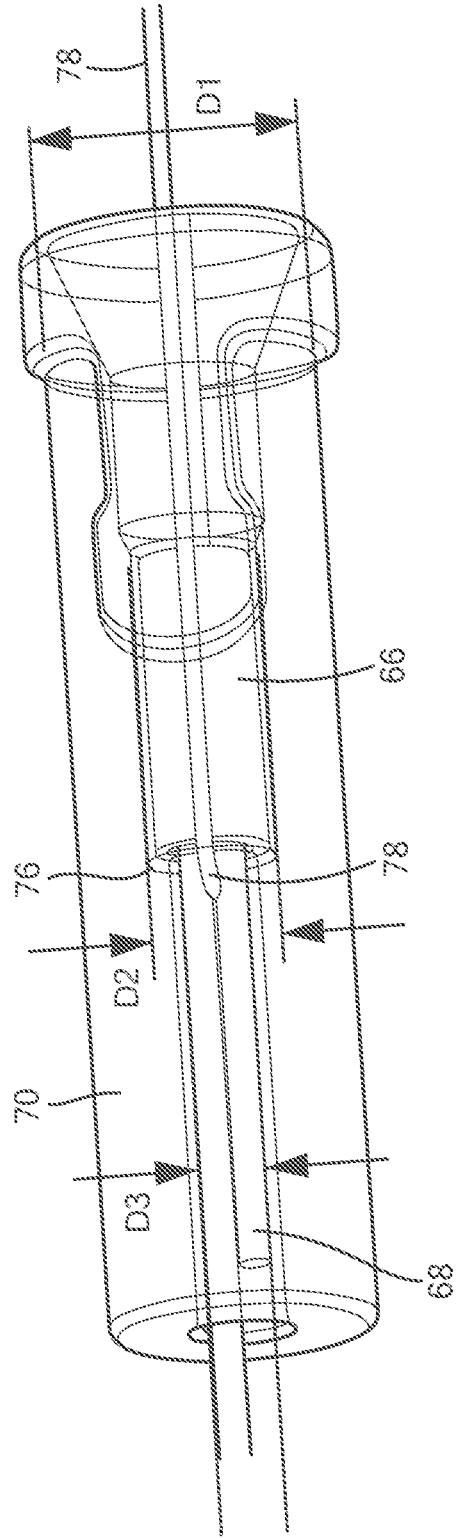

FIG. 15F schematically shows a transparent view of the delivery housing 72 of FIGS. 15A-15E. The cinch lock 66 is retracted and settled into the lumen 73 of the anchor 70. As shown, the maximum dimension D3 of the suture capturing portion 68 is smaller than the diameter D1 of the delivery housing 72 and the dimeter D2 of the lumen 73 (particularly the diameter D2 of the lumen 73 at the point where the cinch lock 66 forms an interference fit with the lumen 73, such as the shoulder 76). It should also be understood from FIGS. 15A and 15F that, in various embodiments, the capturing portion 68 dimension D3 may expand to greater than a diameter of the lock 66 when extended. Similarly, the capturing portion 68 dimension D3 may return to smaller than a diameter of the lock 66 when retracted.

Figure 15G:
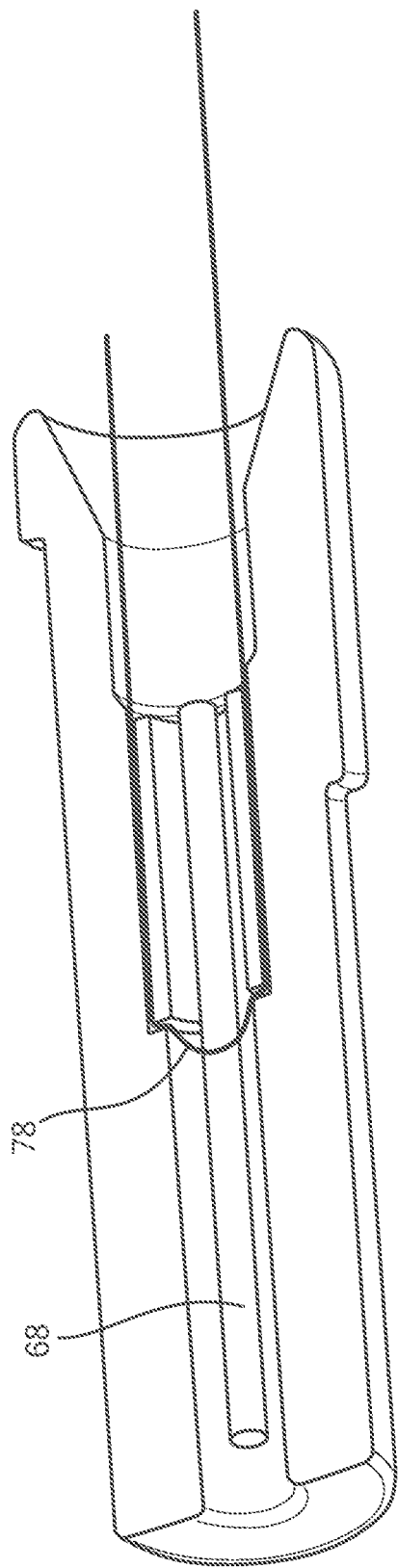

FIG. 15G schematically shows a cut-open view of the delivery housing 72 of FIGS. 15A-15E after the snare wire 68 is disengaged from the locking mechanism. Snare wire 68 disengages from crimp formed by lock 66 when pulling the pull wire 60 with the handle slide 56. The crimp and short wire 68 of the hook may remain in the anchor 70, while the suture 78 is jammed and deformed between the snare crimp formed by the lock 66 and anchor housing 70.

Figure 16:
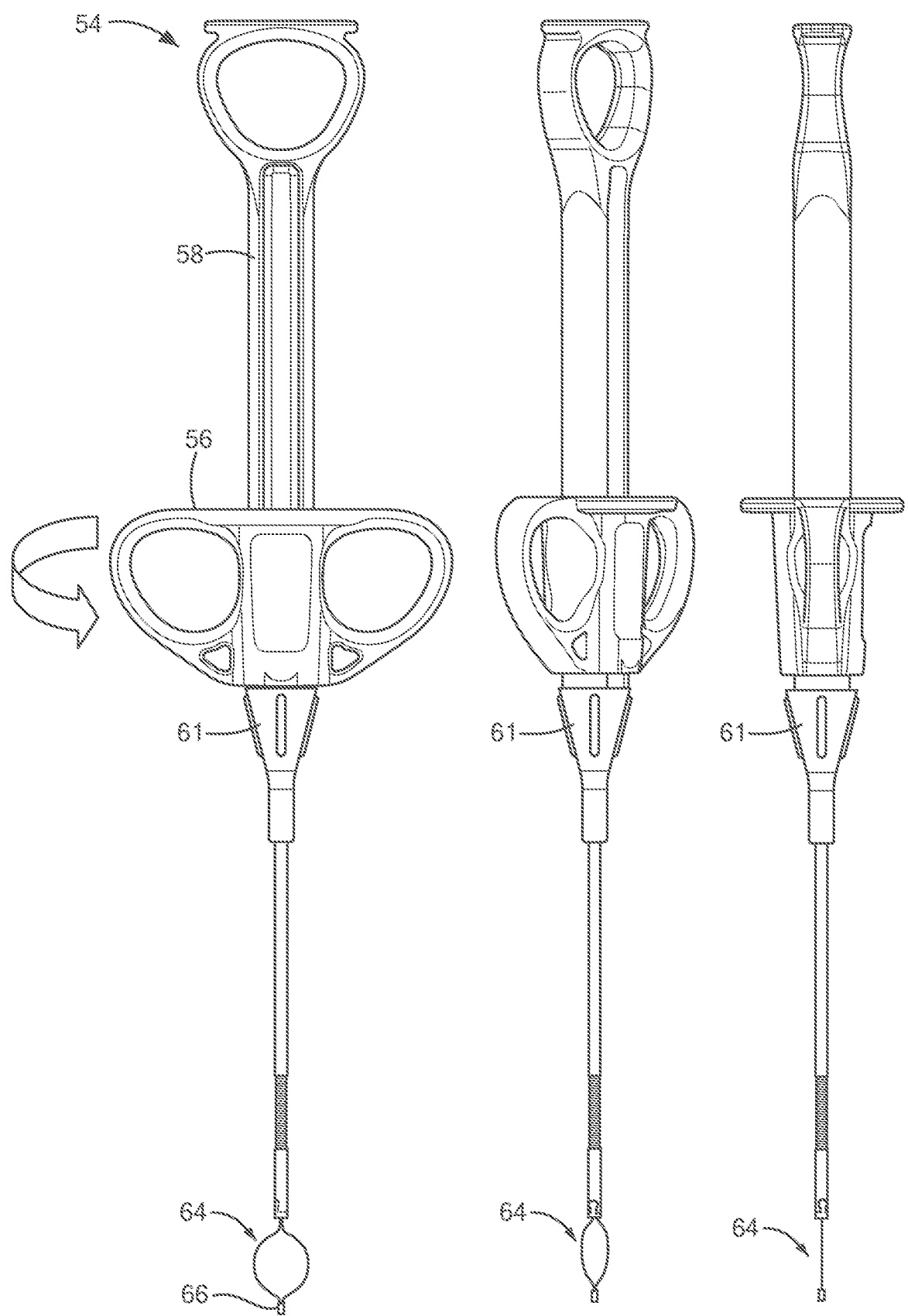
FIG. 16 schematically shows a rotation feature of the cinching device in accordance with illustrative embodiments of the invention.

FIG. 16 schematically show a rotation feature of the cinching device 54 in accordance with illustrative embodiments of the invention. As described previously, the cinching device 54 may be coupled with the endoscope 18. In illustrative embodiments, the handle 51 may be rotated (e.g., with respect to the coupler 61) to rotate the cinch 64. As shown, the coupler 61 does not rotate. In some embodiments, the coupler 61 may couple with the accessory port 37. However, in some other embodiments, the coupler 61 does not couple with the accessory port 37. The coupler 61 maintains its orientation (e.g., relative to the endoscope 18) as the handle 51 and the cinch 64 rotate (as well as the rod 60). Accordingly, the capture portion 68 is advantageously rotatable to allow easy capture of the suture 78. For example, the rotation allows repositioning the loop of the snare or the direction of the hook to an ideal location to capture the suture 78. To that end, in various embodiments, the pull wire 60 is attached to the handle slider 56, and the outer coil 65 (shown in FIG. 6B) is attached to the coupler 61. This allows relative rotation of the drive wire 60, and thus the cinch 64, relative to the flexible tubing 22 and the coil 65.

In various embodiments, the handle 51 is outside of the working channel 38 and is manipulated by the medical practitioner 14. To go through the working channel 38, the delivery shaft is preferably long for endoscopic procedures (e.g., about 150 cm to about 250 cm).

Figure 17A:
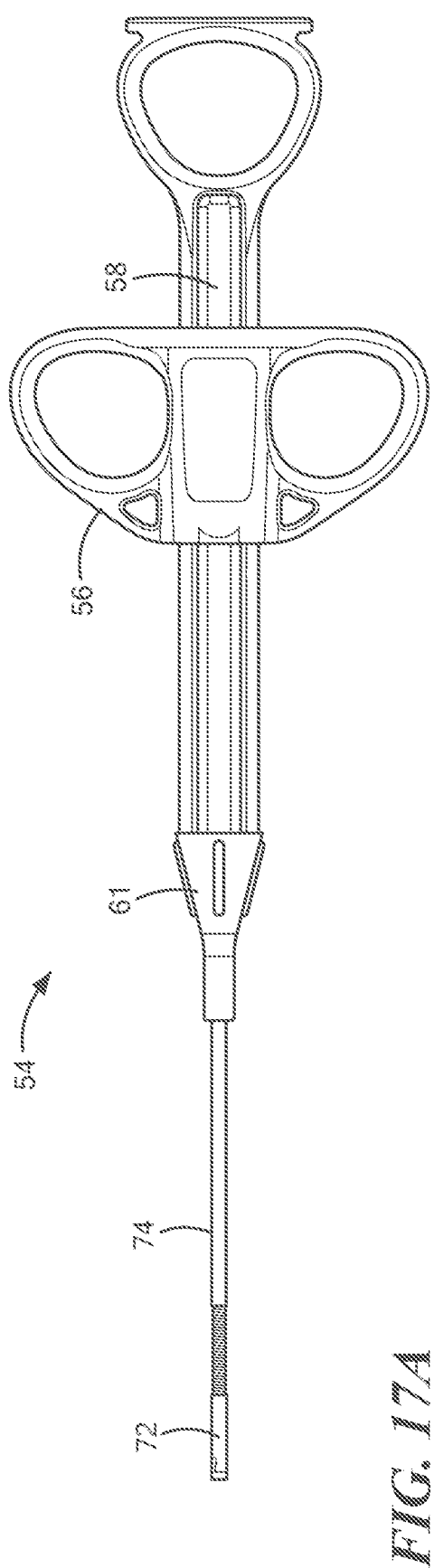
FIGS. 17A-17F schematically show operation of the handle of the cinching device in accordance with illustrative embodiments of the invention.
Figure 17B:
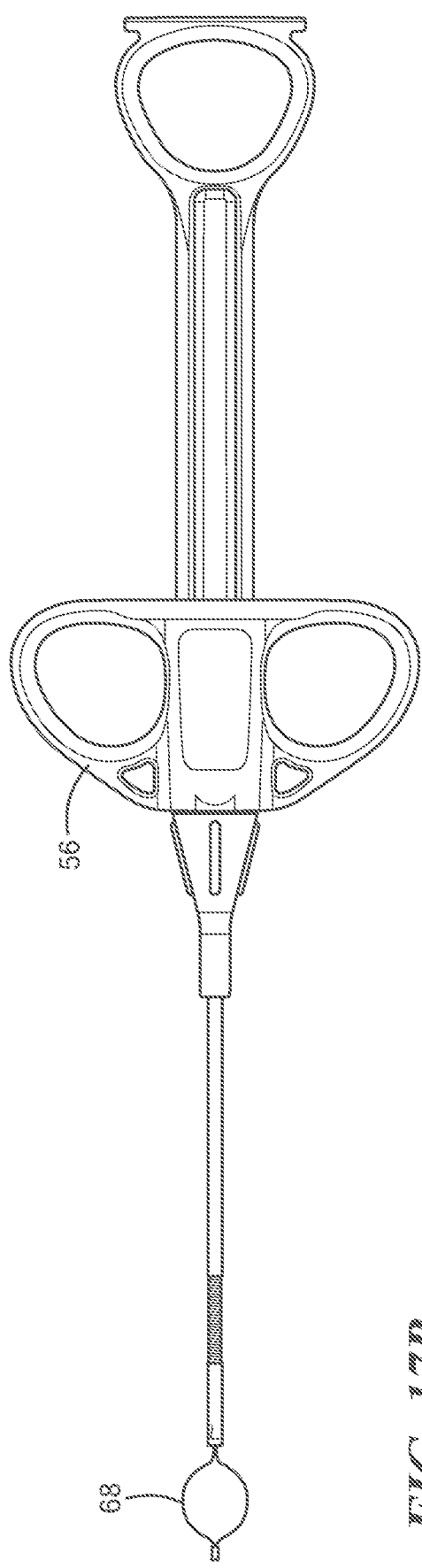
Figure 17C:
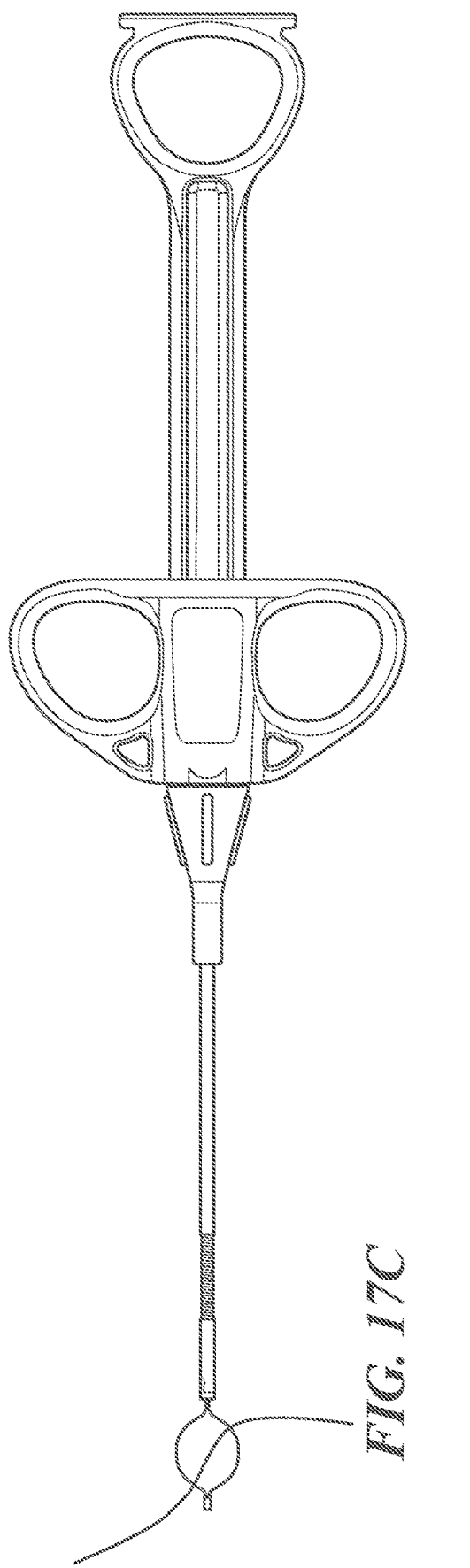

FIGS. 17A-17F schematically show operation of the handle of the cinching device 54 in accordance with illustrative embodiments of the invention. FIG. 17A schematically shows that the capture portion 68 is inside the delivery housing 72. FIG. 17B shows the handle slider 56 fully depressed, and the capture portion 68 extending out of the delivery housing 72. FIG. 17C schematically shows the suture 78 captured. For example, in the case of a snare, illustrative embodiments use the needle to pass the suture 78 through the snare 68. In the case of snare hook, illustrative embodiments use the hook 68 to capture the suture 78. Although not shown, the handle 51 may be rotated to assist with capturing the suture 78.

Figure 17D:
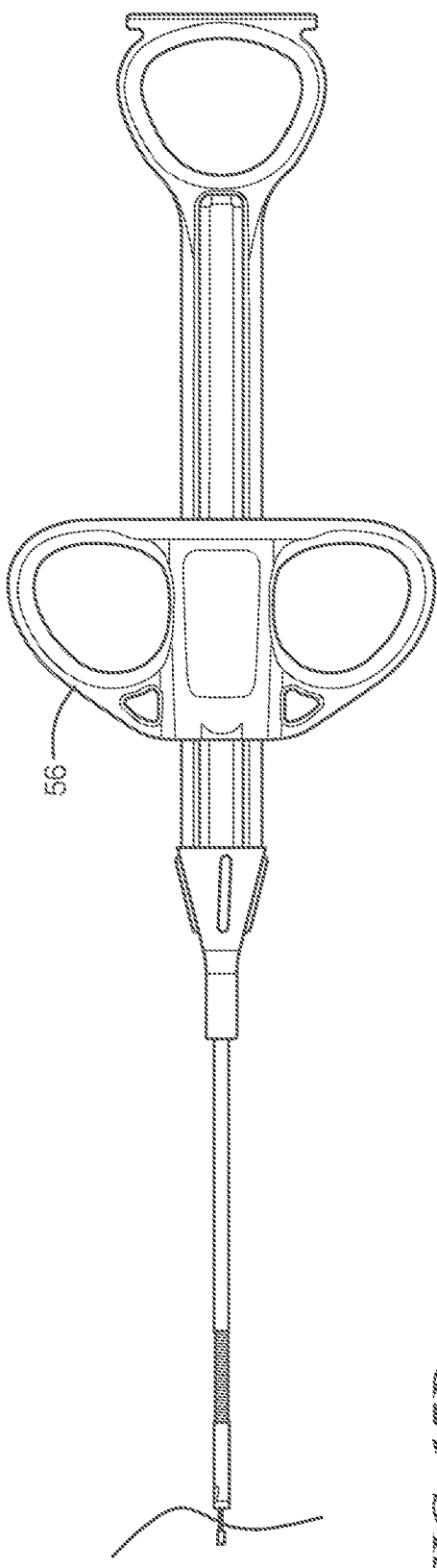
Figure 17E:
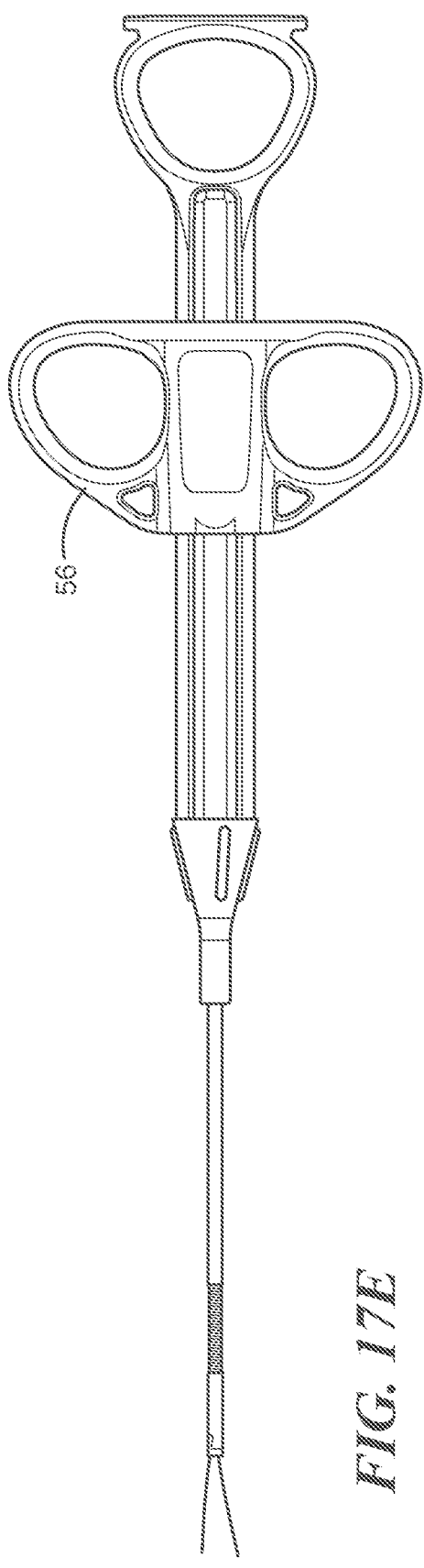
Figure 17F:
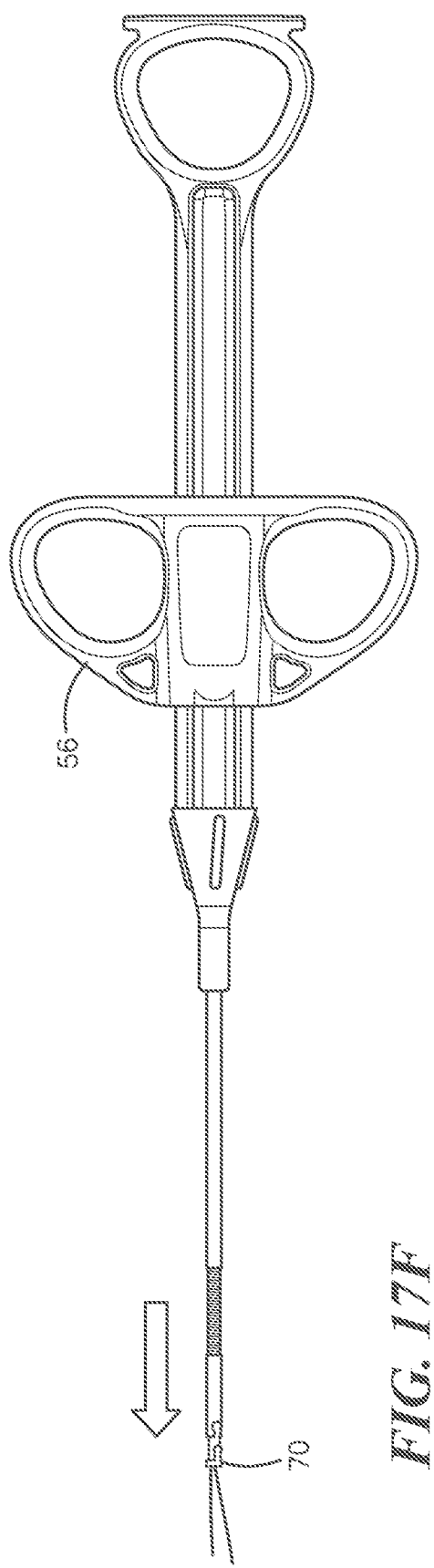

FIG. 17D schematically show that the capturing portion 68 is partially retracted inside the delivery housing 72 to begin bringing the suture 78 inside the anchor 70. As shown, the handle slider 56 is partially retracted to partially retract the is capturing portion 68. FIG. 17E schematically shows the handle slider 56 retracted further. The suture 78 is thus jammed between the crimp and the anchor 70. As the pull wire 60 is pulled further, the snare wires or a portion thereof are uncoupled (e.g., broken away) from the crimp. FIG. 17F schematically shows the cinch lock 66 being deployed by pressing the handle slider 56 again to cause the drive wire 60 to deposit the anchor 70.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Although the above discussion discloses various exemplary embodiments of the invention, it should be apparent that those skilled in the art can make various modifications that will achieve some of the advantages of the invention without departing from the true scope of the invention.

What is claimed is:

1. A method of cinching a suture, the method comprising:
   providing a cinch comprising:
      a suture capturing portion configured to capture a suture,
      a cinch lock coupled with the suture capturing portion, and
      a cinch anchor having a lumen;
   extending the suture capturing portion out of the lumen to capture the suture;
   retracting the suture capturing portion into the lumen of the cinch anchor; and
   cinching the suture between the cinch lock and the cinch anchor.

2. The method as defined by claim 1, further comprising:
   deploying the cinch anchor within a patient by pressing the handle to overcome a threshold deployment force; and
   disengaging the suture capturing portion from the cinch lock by pulling on the handle to overcome a threshold disengagement force.

3. The method as defined by claim 1, further comprising:
   positioning the cinch into a working channel of an endoscope; and
   extending the suture capturing portion out of the working channel of the endoscope.

4. The method as defined by claim 1, wherein the suture capturing portion includes a snare.

5. The method as defined by claim 1, wherein the suture capturing portion is flexible.

6. The method as defined by claim 1, wherein the suture capturing portion includes a wire.

7. The method as defined by claim 1, further comprising: stitching the suture in the patient prior to capturing the suture.

8. The method as defined by claim 1, wherein the suture is cinched by an interference fit between the cinch anchor and the cinch lock.

9. The method as defined by claim 1, wherein the cinch is coupled with a delivery shaft of a hand-held cinching device, the method comprising positioning the delivery shaft in an accessory port of an endoscope.

10. The method as defined by claim 1, further comprising rotating the suture capturing portion relative to the lumen.

11. A cinching system comprising:
    an endoscope having an insertion tube, the insertion tube having at least one working channel;
    a cinching device comprising:
       a handle movably coupled with a flexible drive wire, the handle configured to move the drive wire proximally or distally within a working channel of an endoscope;
       a suture capturing portion coupled with a distal end of the drive wire, wherein movement of the drive wire in a distal direction causes movement of the suture capturing portion in a distal direction;
       a cinch anchor having a lumen through which the suture capturing portion travels;
       a cinch lock coupled with the suture capturing portion, wherein movement of the suture capturing portion in a distal direction causes movement of the cinch lock in a distal direction and movement of the suture capturing portion in a proximal direction causes movement of the cinch lock in a proximal direction,
       wherein an inner diameter of the lumen is configured to provide an interference fit with the cinch lock when the cinch lock enters the lumen.

12. The cinching system of claim 11, wherein the cinch lock is disengageably coupled with the suture capturing portion.

13. The cinching system of claim 11, wherein the cinch anchor is disengageably coupled with a delivery housing.

14. The cinching system of claim 11, further comprising: a suture stitched in a patient.

15. The cinching system of claim 11, wherein the cinch anchor has a fastening portion configured to couple the cinch anchor with a delivery housing.

16. A cinching device comprising:
    a delivery housing configured to fit within a working channel of an endoscope;
    a cinch anchor coupled with the delivery housing, the cinch anchor having a lumen extending from a proximal end to a distal end;
    a suture capturing portion movably positioned in the lumen, the suture capturing portion configured to capture a suture;
    a cinch lock coupled with the suture capturing portion, wherein the cinch lock is configured to provide an interference fit with an inner diameter formed by the lumen when the cinch lock enters the lumen.

17. The cinching device of claim 16, further comprising a user-manipulated drive wire coupled with the suture capturing portion.

18. The cinching device of claim 16, wherein the suture capturing portion is flexible.

19. The cinching device of claim 16, wherein the suture capturing portion includes a wire.

20. The cinching device of claim 16, wherein the suture capturing portion includes a snare.

* * * * *